United States Patent [19]

Halabisky et al.

[11] Patent Number: 5,837,627
[45] Date of Patent: Nov. 17, 1998

[54] FIBROUS WEB HAVING IMPROVED STRENGTH AND METHOD OF MAKING THE SAME

[75] Inventors: Donald D. Halabisky, Tacoma; Hugh West, Seattle; Andre S. Hajnal, Federal Way; Terry M. Grant, Auburn, all of Wash.

[73] Assignee: Weyerhaeuser Company, Federal Way, Wash.

[21] Appl. No.: 669,406

[22] Filed: Jan. 13, 1997

Related U.S. Application Data

[63] Continuation-in-part of Ser. No. 399,408, Mar. 6, 1995, abandoned.

[51] Int. Cl.$^6$ ................................................. A61F 13/15
[52] U.S. Cl. ....................... 442/385; 442/393; 442/394; 162/146; 162/148; 162/157.6; 162/164.1; 604/366; 604/368; 604/378
[58] Field of Search ................................. 162/146, 148, 162/157.6, 158, 164.1; 442/385, 393, 394; 604/365, 366, 368, 378

[56] References Cited

U.S. PATENT DOCUMENTS

| | | |
|---|---|---|
| 2,277,049 | 3/1942 | Reed . |
| 2,277,050 | 3/1942 | Reed et al. . |
| 3,053,609 | 9/1962 | Miller . |
| 3,365,354 | 1/1968 | Britton . |
| 3,426,764 | 2/1969 | Pearman . |
| 3,574,523 | 4/1971 | Hudson, Jr. et al. . |
| 3,621,764 | 11/1971 | Muller et al. . |
| 3,658,626 | 4/1972 | Berger et al. ............... 156/441 |
| 3,800,676 | 4/1974 | Levers et al. . |
| 3,900,037 | 8/1975 | Horsewell et al. . |
| 3,930,077 | 12/1975 | Levers et al. ............... 427/384 |
| 3,933,160 | 1/1976 | Gerady . |
| 4,256,524 | 3/1981 | Hare . |
| 4,257,344 | 3/1981 | Coq . |
| 4,274,914 | 6/1981 | Keith et al. . |
| 4,536,432 | 8/1985 | Holtman . |
| 4,590,114 | 5/1986 | Holtman . |
| 4,681,577 | 7/1987 | Stern et al. . |
| 4,685,914 | 8/1987 | Holtman . |
| 5,022,964 | 6/1991 | Crane et al. . |
| 5,217,445 | 6/1993 | Young et al. . |
| 5,231,122 | 7/1993 | Palumbo et al. . |
| 5,316,601 | 5/1994 | Hebbard et al. . |
| 5,316,705 | 5/1994 | McNair, Jr. et al. . |
| 5,432,000 | 7/1995 | Young, Sr. et al. . |

FOREIGN PATENT DOCUMENTS

| | | |
|---|---|---|
| 949737 | 6/1974 | Canada . |
| 1257520 | 3/1986 | Canada . |
| 0 548 902 A1 | 6/1993 | European Pat. Off. . |
| 2038188 | 1/1971 | France . |
| 2324247 | 4/1977 | France . |
| 1421543 | 10/1968 | Germany . |
| 230118 | 1/1974 | Germany . |
| 1427975 | 3/1976 | United Kingdom . |
| 2012553 | 8/1979 | United Kingdom . |
| WO 93/18218 | 9/1993 | WIPO . |

OTHER PUBLICATIONS

Schaffer, R.E., and T. van Dorp, "Solvent Bondings of Synthetic Fibres," *American Chemical Society*, pp. 249–257 (1973).

Le Solvent Latent pour le Liage des Fibres Acryliques, *De Tex–Textilis*, 1:2–24 (1975).

Smith, E., "Cellulose Acetate Fibrets: a Fibrillated Pulp with High Surface Area, " *Tappi Journal*, pp. 185–187 (1987).

Holliday, T.M., "Bonding Nonwovens: the Methods," *Nonwovens Conference*, pp. 335–341 (1993).

Duckett, K.E., G. Bhat, and H. Suh, "Compostable Nonwovens from Cotton/Cellulose Acetate Blends," *Nonwovens Confernce/TAPPI Proceedings*, pp. 89–96 (1995).

*Primary Examiner*—Christopher Raimond
*Attorney, Agent, or Firm*—Christensen O'Connor Johnson & Kindness PLLC

[57] ABSTRACT

A web of fibers is bound together by a bonding medium that has been activated by partially solubilizing the bonding medium with a solvent therefor. The fibers are insoluble in the bonding medium. As the bonding medium is partially solubilized, it becomes tacky and flows into contact with the fibers and with itself Thereafter, the solvent is absorbed by the bonding medium, allowing the bonding medium to resolidify and bond the fibers in a matrix, increasing the web strength.

62 Claims, 5 Drawing Sheets

FIBROUS WEB HAVING IMPROVED STRENGTH AND METHOD OF MAKING THE SAME

RELATED APPLICATIONS

This application is a continuation-in-part of prior copending patent application Ser. No. PCT/US96/03029, filed on Mar. 4, 1996, which, in turn, claims priority from, patent application Ser. No. 08/399,408, filed Mar. 6, 1995, now abandoned, the benefit of the filing date of which is claimed under 35 U.S.C. § 120.

FIELD OF THE INVENTION

The present invention relates to fibrous webs and methods for making the same, more particularly to webs containing pulped cellulosic fibers, and most particularly to pulped cellulosic fiber webs having an internally bonded matrix that increases the wet and/or dry strength of a construct made from the web.

BACKGROUND OF THE INVENTION

Wood pulp fibers, are used in a variety of absorbent products. The wood pulp fibers are formed into webs, which are then placed in various constructs, for example, diapers, incontinence products, and feminine hygiene products. Because webs of wood pulp fibers inherently do not have great wet or dry strength, especially in tension, various methods have been devised for improving the wet and dry strength of the webs so that the end product into which they are incorporated has superior strength characteristics.

Often webs produced of wood pulp fibers are produced using the conventional air laid process to provide a low-density, fluffy product. The strength of these air laid webs has been increased by a variety of techniques. One such technique is to spray a latex on one side of the web after it is formed. That web is dried and then turned over. The latex is then sprayed on the back side of the web and also dried. Normally the latexes used are about fifty percent solids (the balance being water) and are sprayed on the webs at a rate of ten (10) to thirty (30) percent based on the fiber weight. This requires a significant quantity of water to be removed from the web during processing. Also, to develop wet strength, formaldehyde is often included in the latex formulation to cross-link and insolubilize the resin after it is dried. While this process produces a strengthened wood pulp web, it has several disadvantages. These include substantial energy required to dry the latex; a significant capital cost for latex storage, spraying, and drying; environmental and handling problems associated with latex and formaldehyde; and high latex costs because of the quantity needed to provide an adequate strength increase. In addition, the latex overspray inherently resulting from the spraying eventually coats the area surrounding the spray apparatus requiring significant housekeeping effort and expense. Finally, a latex can only be used on thin products because the latex does not penetrate much below the surface of the web.

Thermal bonding has also been used to strengthen air laid webs. In this process, thermally sensitive fibers or powders are added to the fiber system before the mixture is laid into a web. These fibers are fused by passing them through an oven or a hot calender. Again, this process produces a significant increase in wet and dry strength. However, the process has significant disadvantages including the high capital cost of thermal bonding ovens with accurate temperature control systems, the time required to thermally bond which usually creates a bottleneck in production, and fiber and dust buildup in the ovens which can cause fire hazards. Moreover, existing diaper production lines do not have the physical space required for bulky bonding ovens. Also, thermal bonding materials are not generally biodegradable, a highly desirable attribute for disposable products. Thermal bonding also detracts from the absorbency because thermal bonding materials are generally hydrophobic.

SUMMARY OF THE INVENTION

In accordance with a broad aspect of the present invention, an article is provided comprising a web of pulped cellulosic fibers that are loosely interspersed with each other. A bonding medium is placed in contact with at least some of the pulped cellulosic fibers for the purpose of bonding at least some of the pulped cellulosic fibers together to form a strengthened web. The bonding occurs through the solubilizing action of a solvent for the bonding medium. The pulped cellulosic fibers are insoluble in the solvent. The solvent has a limited volatility of up to 29 kPa at 25° C. The bonding medium is placed in contact with the fibers by, for example, dispersing the bonding medium throughout the pulped cellulosic fiber web, or placing a layer of bonding medium on the pulped cellulosic fiber web, or placing the bonding medium in contact with only certain of the pulped cellulosic fibers. When the bonding medium is contacted by the solvent, the surface of the bonding medium is at least partially solubilized, rendering it tacky so that the bonding medium adheres to at least some of the pulped cellulosic fibers. The solvent, however, is present in an amount insufficient to completely solubilize the bonding medium. Instead, after partially solubilizing the surface of the bonding medium, the solvent is thereafter dissipated, for example, by being sufficiently absorbed by the bonding medium, to allow the surface of the bonding medium to resolidify, resulting in permanent bonding of the bonding medium either to itself and/or at least some of the cellulosic fibers. The entire process may also be facilitated with heat. This bonding mechanism significantly increases both the wet and dry strength of a resulting web without the attendant disadvantages of prior art strengthening methods.

In a preferred embodiment, the bonding medium comprises second fibers that are either the bonding medium alone or are fibers coated with the bonding medium. These second fibers are either interspersed throughout the pulp fibers in the web, or are layered on one or both sides of the pulp fibers in the web. When the solvent contacts the second fibers, the surfaces of the second fibers are partially solubilized and become tacky. The tacky surfaces of the second fibers contact and adhere to each other and to the pulp fibers. As the solvent is dissipated, as by being absorbed by the second fibers, the surfaces of the second fibers solidify, forming permanent bonds between the pulp fibers and the second fibers. The resulting bonded web exhibits superior strength characteristics that are useful, for example, in absorbent constructs such as diapers, feminine hygiene products, and incontinence products. The bonding medium may also be in the form of a powder or particle. Again, the powder or particle may be the bonding medium alone, or may be a powder or particle coated with the bonding medium. The powder or particles may be interspersed with the wood pulp fibers in the web.

Also provided in accordance with the present invention are processes for forming a web having improved strength characteristics. Broadly, the bonding medium, preferably in the form of fibers comprising the bonding medium, is combined with a web of randomly oriented pulped cellulosic fibers that are interspersed with each other. The bonding medium may be combined with the pulped cellulosic fiber web by either mixing and interspersing the bonding medium with the pulped cellulosic fibers or by layering the bonding medium and the web. The solvent for the bonding fibers is also introduced into the web so that it can partially solubilize the surface of the bonding fibers. As it does so, the surfaces of the bonding fibers becomes tacky causing the bonding fibers to adhere to themselves and to the pulped cellulosic fibers. The amount of solvent used is limited so that it cannot completely solubilize the bonding fibers, and so that it can dissipate to allow the surfaces thereof to resolidify and form a permanent bond with the pulped cellulosic fibers. The solvent can be introduced into the web by first combining it with all or part of the cellulosic fibers. Alternatively, the solvent can be sprayed on the web after the bonding fibers are in contact with the pulped cellulosic fibers. When the solvent is combined with the cellulosic fibers, the fibers can be stored for a period of time and can be transported to the place of use before being combined with the bonding medium.

The pulped cellulosic fibers may be wood pulp fibers, or fibers pulped from other agricultural products such as straw, kenaf or similar material.

BRIEF DESCRIPTION OF THE DRAWINGS

A better understanding of the invention can be derived by reading the ensuing specification in conjunction with the accompanying drawings wherein.

DETAILED DESCRIPTION OF THE INVENTION

Figure 1:
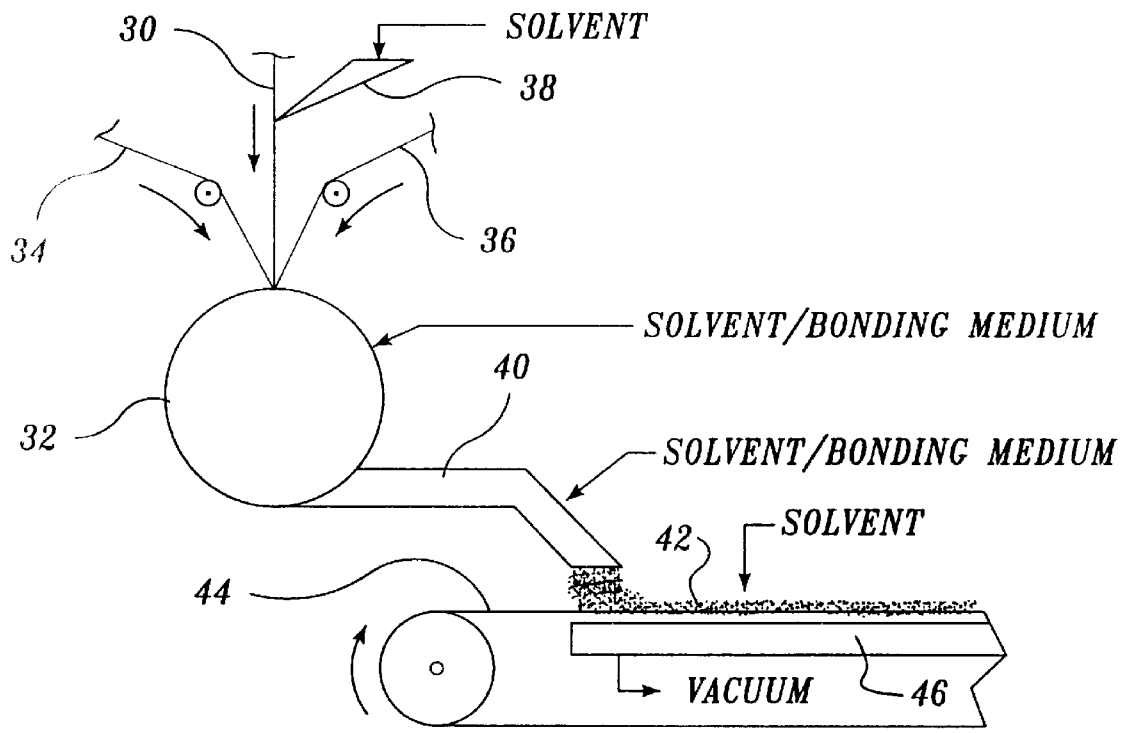
FIG. 1 is a schematic view of one process for producing the material of the present invention.

The present invention provides a strengthened web containing pulped cellulosic fibers, a bonding medium and a solvent that partially solubilizes the bonding medium. In one preferred form of the invention, the bonding medium comprises solvent soluble fibers that are dispersed unevenly throughout the web of pulped cellulosic fibers. In another preferred form of the invention, the solvent soluble fibers are evenly dispersed throughout the web of pulped cellulosic fibers. In a third preferred form, the solvent soluble fibers are in a layer on one side of the web, preferably the top side. In a fourth preferred form, the solvent soluble bonding medium is localized at the interface of a web of pulped cellulosic fibers and another material such as a tissue or nonwoven coverstock.

The solvent can be contacted with the bonding fibers before, after, and/or during the formation of the web. The amount of solvent is chosen such that at least some of the surfaces of the bonding fibers are partially solubilized. When partially solubilized, the surface layer of the bonding medium becomes tacky. It can then flow onto surfaces that it contacts, including both the bonding fibers themselves and the pulped cellulosic fibers. As it flows onto these surfaces, it wets the surfaces. The solvent is applied in an amount insufficient to completely solubilize the fibers and is also applied in an amount such that the solvent is eventually dissipated, for example by being absorbed into the soluble fibers or into the pulped cellulosic fibers. As the solvent is absorbed into the soluble fibers, the surface concentration of the solvent decreases and allows the surfaces of the fibers to resolidify. As they resolidify they bond to themselves and to other materials including the pulped cellulosic fibers at the contact and wetting points. Thus a strong matrix of pulped cellulosic fibers interconnected with bonding fibers is produced. The web thus produced exhibits a significantly greater dry integrity and, depending on the bonding medium and solvent, greater wet integrity than a web composed of pulped cellulosic fibers alone. One expression of integrity is that the material maintains its structure, shape or conformation under load. Another expression of integrity is the dry or wet strength of the material.

The pulped cellulosic fibers used in accordance with the present invention are conventionally employed to form a web for use, for example, in absorbent articles. The pulped cellulosic fibers are insoluble in the solvent used to partially solubilize the bonding medium. A wide variety of pulped cellulosic fibers, derived from wood and non-wood sources, can be used. Wood pulp is most commonly employed because of its availability and price. Therefore, cellulosic fibers derived primarily from wood pulp are most preferred. Suitable wood pulp fibers for use with the invention can be obtained from well-known chemical processes. The pulp fibers may also be processed by chemical methods, thermomechanical methods, chemithermomechanical methods, or combinations thereof The preferred pulp fiber is produced by chemical methods, either sulfate or sulfite. The preferred starting material is prepared from long-fiber coniferous wood species such as southern pine, Douglas fir, spruce, and hemlock. Other chemical pulps made from short or long fibered wood species, ground wood fibers, recycled or secondary wood pulp fibers, and bleached and unbleached wood pulp fibers can be used. Short wood fibers are produced from hardwood species, such as eucalyptus, using known chemical processes or from any wood species using mechanical or chemithermomechanical methods. Details of the production of wood pulp fibers are well-known to those skilled in the art. Such fibers are commercially available from a number of companies, including Weyerhaeuser Company, the assignee of the present invention. For example, suitable cellulose fibers produced from southern pine that are usable with the present invention are manufactured by Weyerhaeuser Company under the designations CF416, NF405, NB416 and CMC518.

Straw, flax, kenaf or similar materials may also be used as a starting material for the pulped cellulosic fibers.

The wood pulp fibers of the present invention can also be pretreated prior to use with the present invention. This pretreatment may include physical treatment, such as subjecting the fibers to steam, or chemical treatment, for example, cross-linking the cellulose fibers using any of a variety of cross-linking agents such as dimethyldihydroxyethyleneurea. Cross-linking the fibers, for example, increases their resiliency, and thereby can improve their absorbency. The fibers may also be twisted or crimped, as desired. Suitable cross-linked pulp produced from southern pine are manufactured by Weyerhaeuser Company under the designation NHB416.

Although not to be construed as a limitation, examples of pretreating fibers include the application of fire retardants to the fibers, such as by spraying the fibers with fire-retardant chemicals. Specific fire-retardant chemicals include, by way of example, sodium borate/boric acid, urea, urea/phosphates, etc. In addition, the fibers may be pretreated with surfactants or other liquids, such as water or solvents, which modify the surface of the fibers. These are known as softened or debonded fibers. Other pretreatments include exposure to antimicrobials, pigments and densification or softening agents. Fibers pretreated with other chemicals, such as thermoplastic and thermosetting resins also may be used. Combinations of pretreatments also may be employed with the resulting pretreated fibers then being subjected to the application of the binder as explained below.

Cellulosic fibers treated with particle binders and/or densification/softness aids known in the art can also be employed as the pulped cellulosic fibers in accordance with the present invention. The particle binders can serve to attach other materials, such as superabsorbent polymers, to the cellulosic fibers. Cellulosic fibers treated with suitable particle binders and/or densification/softness aids and the process for combining them with cellulose fibers are disclosed in the following U.S. patents and patent applications: (1) Ser. No. 07/931,059, filed Aug. 17, 1992, entitled "Polymeric Binders for Binding Particles to Fibers"; (2) Ser. No. 07/931,277, filed Aug. 17, 1992, entitled "Non-Polymeric Organic Binders for Binding Particles to Fibers"; (3) U.S. Pat. No. 5,300,192, entitled "Wet Laid Fiber Sheet Manufacturing With Reactivatable Binders for Binding Particles to Fibers"; (4) U.S. Pat. No. 5,352,480, entitled "Method for Binding Particles to Fibers using Reactivatable Binders"; (5) U.S. Pat. No. 5,308,896, entitled "Particle Binders for High-Bulk Fibers"; (6) Ser. No. 07/931,279, filed Aug. 17, 1992, entitled "Particle Binders that Enhance Fiber Densification"; (7) Ser. No. 08/107,469, filed Aug. 17, 1993, entitled "Particle Binders"; (8) Ser. No. 08/108,219, filed Aug. 17, 1993, entitled "Particle Binding to Fibers"; (9) Ser. No. 08/107,467, filed Aug. 17, 1993, entitled "Binders for Binding Water Soluble Particles to Fibers"; (10) Ser. No. 08/108,217, filed Aug. 17, 1993, entitled "Particle Binders"; (11) Ser. No. 08/108,218, filed Aug. 17, 1993, entitled "Particle Binding to Fibers"; and (12) U.S. Pat. No. 5,447,977, entitled "Particle Binders for High-Bulk Fibers," all expressly incorporated herein by reference. One example of a suitable densification/softness aid is a mixture of 70% sorbitol and 30% glycerin. The pulp is treated with sorbitol and glycerin by spraying the pulp sheet with the mixture and passing the sheet through a toll coater, or other means of adding a liquid to a pulp sheet familiar to those skilled in the art.

The soluble bonding medium utilized in accordance with the present invention can be incorporated with the pulped cellulosic fibers, either in fiber form, or as particles or granules. If desired, the bonding medium can also be coated onto solvent insoluble fibers, such as cellulosic fibers, which can then be distributed throughout the matrix of pulped cellulosic fibers. It is presently preferred that the bonding medium comprise a fiber and be mixed with the pulped cellulosic fibers during, for example, the formation of a fluff web by conventional air laid processes.

The solvents employed in accordance with the present invention must of course be capable of partially solubilizing the bonding medium as described above. The solvents must be able to partially dissipate or migrate from the surface of the bonding medium to allow the bonding medium to resolidify after partial solubilization. Nonvolatile solvents may be dissipated in most part by absorption into the bonding medium. It is preferred that the solvent be of limited volatility, so that little or no solvent will be lost to the atmosphere. By limited volatility it is meant that the solvent has a vapor pressure of 29 kPa or less at 25° C. Using a solvent of limited volatility may mitigate precautions usually necessary to control volatiles, and reduces the amount of solvent required to partially solubilize the bonding medium. In addition, use of solvents of limited volatility may eliminate the attendant processing problems encountered with volatile solvents, many of which are flammable and must be handled with care. The use of solvents of limited volatility may also reduce environmental problems. Furthermore, it is desirable for solvents to be nontoxic and capable of being dissipated from the surface of the bonding medium without adversely affecting the overall strength of the bonding medium.

Preferred bonding mediums and solvents of limited volatility are listed in the table set forth below.

| Bonding Medium | Solvent |
| --- | --- |
| cellulose acetate | triacetin |
| | propane diol diacetate |
| | propane diol dipropionate |
| | propane diol dibutyrate |
| | triethyl citrate |
| | dimethyl phthalate |
| | dibutyl phthalate |
| cellulose nitrate | triacetin |
| cellulose butyrate | triacetin |
| vinyl chloride/vinyl acetate copolymer | triacetin |
| cellulose fibers coated with polyvinyl acetate | triacetin |

Of the several bonding mediums listed, cellulose acetate is the most preferred. During manufacture of cellulose acetate fibers, a finish is usually applied to the fibers. Many times this finish is in the form of an oil. The presence of the finish sometimes detracts from the performance as a bonding medium. The presence of a finish may adversely affect the development as well as the strength of the bonds. It has been found that when the bonding fibers are as straight as possible, as opposed to curled or kinked, they provide more contact points with the cellulosic fibers, and thus the final web will develop better strength. Similarly, when the bonding fibers are as long as is reasonably possible, the strength of the final web is increased. In addition to the foregoing, cellulose ethers and other cellulose esters may also be used as bonding medium. Acetylated pulp fibers may also be used as bonding medium and may be substituted with any number of acetyl groups. A preferred degree of substitution (D.S.) would be 2 to 3, and a most preferred D.S. would be 2.4.

The solvents can be added in varying amounts. Strength is adversely affected if too little or too much solvent is added. At a cellulose acetate/pulp weight ratio of 10/90, it has been found that the solvents, and particularly triacetin, provide good strength when added in amounts ranging from 6% to 17%, and most preferably in the range of 9% to 14%, based on the weight of pulp fiber present.

The preferred forms of the solvents propane diol diacetate, dipropionate, and dibutyrate are the 1, 2 and 1, 3 forms. Other suitable solvents that will work in accordance with present invention are butyl phthalyl butyl glycolate, N-cyclohexyl-p-toluenesulfonamide, diamyl phthalate, dibutyl phthalate, dibutyl succinate, dibutyl tartrate, diethylene glycol dipropionate, di-(2-ethoxyethyl)adipate, di-2-ethoxyethyl)phthalate, diethyl adipate, diethyl phthalate, diethyl succinate, diethyl tartrate, di-(2-methoxyethyl) adipate, di-(2-methoxyethyl)phthalate, dimethyl phthalate, dipropyl phthalate, ethyl o-benzoylbenzoate, ethyl phthalyl ethyl glycolate, ethylene glycol diacetate, ethylene glycol dibutyrate, ethylene glycol dipropionate, methyl o-benzoylbenzoate, methyl phthalyl ethyl glycolate, N-o & p-tolylethylsulfonamide, o-tolyl p-toluenesulfonate, tributyl citrate, tributyl phosphate, tributyrin, triethylene glycol diacetate, triethylene glycol dibutyrate, triethylene glycol dipropionate, and tripropionin.

It is also possible to incorporate additives into a web formed in accordance with the present invention. The advantage of incorporating the additives during the web formation is that they will also be attached to the matrix by certain of the solvents and bound in the matrix by the bonding medium. This provides a significant advantage in that the additives can be dispersed and retained throughout the matrix where desired. For example, the additives may be evenly dispersed and retained throughout the matrix. Additives that can be incorporated into the matrix include absorbent capacity enhancing materials such as superabsorbent polymers, adsorbents such as clays, zeolites and activated carbon, brighteners such as titanium oxide, and odor absorbents such as sodium bicarbonate. Solvents can also reduce the dusting caused by the additives or the pulp itself because more of the fines are attached and bound to the matrix by the bonding medium.

A superabsorbent polymer as used herein is a polymeric material that is capable of absorbing large quantities of fluid by forming a hydrated gel. The superabsorbent polymers also can retain significant amounts of water under moderate pressures. Superabsorbent polymers generally fall into three classes, namely, starch graft copolymers, cross-linked carboxymethylcellulose derivatives, and modified hydrophilic polyacrylates. Examples of such absorbent polymers are hydrolyzed starch-acrylonitrile graft copolymer; a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-cross-linking polyacrylic acid, a cross-linked polyacrylate salt, carboxylated cellulose, and a neutralized cross-linked isobutylene-maleic anhydride copolymer. The superabsorbent polymers can be combined with the cellulosic fibers and bonding medium. It is possible to achieve a combination with 75% superabsorbents by weight based on the total weight of fibers and superabsorbent polymer. It is assumed that higher levels can be achieved.

It has also been found that the dry strength of the bonded fiber web can be further increased when superabsorbents are added by first treating the superabsorbents with solvent, for example, triacetin. Solvent amounts on the order of two percent (2%) of the final weight of the superabsorbent and the solvent will leave the superabsorbent flowable. In addition, the superabsorbent retention in the final web is increased. This increased retention may be due to the bonding medium, to physical bonding (encapsulation), hydrogen bonding or a combination of one or more of the three.

A web can be produced in accordance with the present invention in a variety of ways using for example air laid or wet laid web forming techniques known to those of ordinary skill. The webs can vary in density from for example, 0.03 g/cc to 1 g/cc. The amount of bonding medium and solvent employed in a particular web can vary greatly depending upon the processing techniques as well as the desired characteristics of the end product. One of ordinary skill will be able to alter the various proportions of the materials to achieve a desired result. For example, the bonding medium would normally be employed in an amount of one-half to twenty percent (0.5% to 20%) by weight based on the amount of pulped cellulosic fiber present to produce a web which can be incorporated into a diaper in which an increase in wet and dry strength is necessary or desired. When producing a web for use as a wet wipe, the amount of bonding medium could be increased to twenty to twenty-five percent (20% to 25%) or more based on the weight of pulped cellulosic fiber present. This higher concentration of bonding medium will yield a stronger product that will not tear apart when used to wipe surfaces. The amount of solvent combined with the bonding medium will also depend upon a variety of other factors, including the method of application of the solvent, the rate of strength development desired, the final strength desired, and other properties of the products such as absorptive capacity and wicking. Thus the amount of solvent applied can range from five-tenths percent (0.5%) to 25 percent (25%) by weight based upon the total weight of pulped cellulosic fibers.

The solvent can be incorporated into the web of pulped cellulosic fibers and bonding medium before, during or after web formation. For example, the bonding medium, in either fiber or particulate form, and pulped cellulosic fibers can be combined in a hammermill and thereafter air laid. The solvent can then be sprayed on the web. The solvent will penetrate the web, contact and partially solubilize the bonding medium. Thereafter the solvent is absorbed or otherwise dissipated, allowing the bonding medium to resolidify and bond to the pulped cellulosic fibers. This method, however, requires a relatively high level of solvent application to achieve a reasonably good web strength.

It has also been found that the order of combination of the bonding medium and the solvent with the cellulosic fibers affects the hydrophilicity/hydrophobicity of the final web. For example adding triacetin to the pulp and then combining the pulp with cellulose acetate will yield an end product that is hydrophilic. To the contrary, adding triacetin during or after the time the cellulosic fibers and cellulose acetate are combined will yield a hydrophobic web.

Referring now to FIG. 1, one preferred method for combining cellulosic fibers, a bonding medium in the form of a fiber, and solvent therefor is to first produce a wet laid blend sheet 30 of fiber comprising the bonding medium and fluff wood pulp. The wet laid blend sheet is then fed into a hammermill 32 between two conventional fluff pulp sheets 34 and 36 in preparation for air laying the pulp into a web. A conventional brush coater 38 can be used to coat the blend sheet with solvent just before the blend sheet enters the hammermill. The solvent can quickly penetrate the blend sheet because it is relatively thin. The bonding fibers are evenly distributed throughout the pulped cellulosic fibers from the fluff sheet and the blend sheet by the hammermill. The resulting mix of pulped cellulosic and bonding fibers are subsequently passed through a screen, transported by air through a conduit 40, and deposited as a web 42 on either a tissue or porous wire 44. When the bonding fiber surfaces dissolve slowly, fiber tackiness is minimal and bonding does not occur until after the fibers are air laid into a web. A vacuum is applied to the back of the wire 44 through a vacuum box 46 to draw the pulped cellulosic fibers and bonding fibers to it. The solvent then begins to solubilize the surfaces of the bonding fibers, allowing them to flow and contact the pulp fibers. Once the solvent is dissipated as by being fully absorbed by the bonding fibers, the surfaces resolidify, forming a bonding matrix for the pulp fibers.

Figure 2:
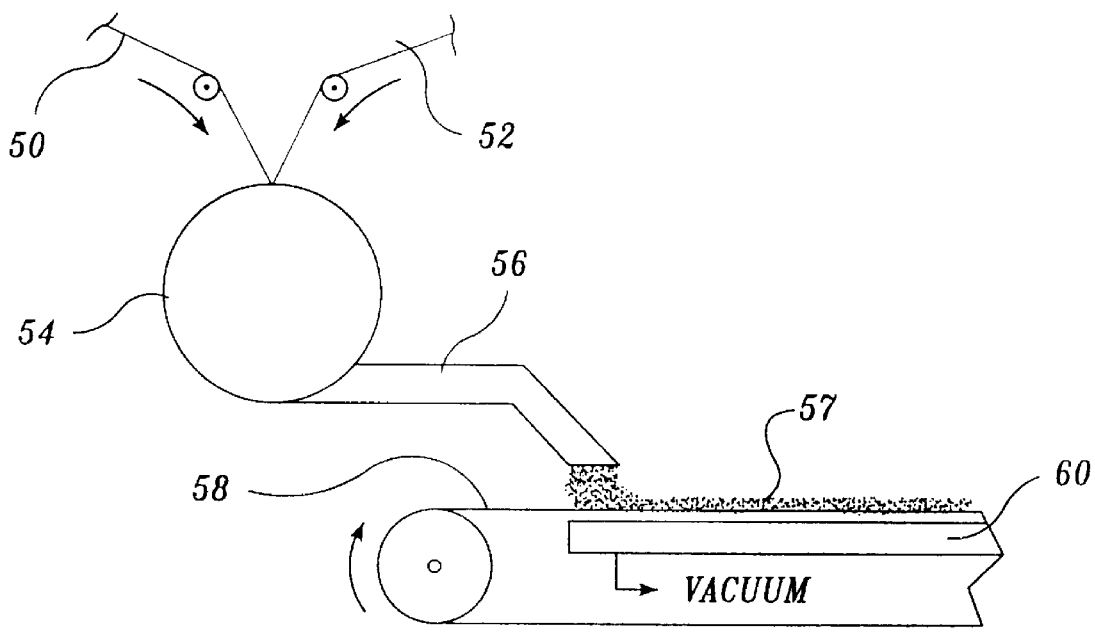
FIG. 2 is a schematic view of another process for producing the material of the present invention.

Referring to FIG. 2, a more preferred method for combining pulped cellulosic fibers, a bonding medium in the form of a fiber, and a solvent therefor is to apply the solvent to a pulp sheet 50 while it is being formed or after it is formed. If a preferred solvent of limited volatility is employed, the pulp sheet can then be transported and/or stored for a period of time before use. Another pulp sheet 52 containing the bonding fibers can be prepared on a paper machine by wet slurrying the bonding fibers with the pulp fibers in the wet end and forming the fibers into a blended pulp sheet. The bonding fibers are distributed throughout the pulp sheet. The solvent containing pulp sheet 50 can then be fed into a hammermill 54 with the pulp sheet 52 containing the bonding fibers in preparation for air laying the pulp into a web. The hammermill thoroughly mixes the fibers containing the solvent with the bonding fibers. The resulting mix of cellulosic and bonding fibers are passed through a screen, transported by air through a conduit 56, and deposited in a web 57 on either a tissue or porous wire 58. As this occurs, the solvent begins to transfer to the bonding fibers from the cellulose fibers. A vacuum is applied to the back of the wire 58 through vacuum box 60 to draw the cellulosic fibers and bonding fibers to it and form a compacted web. Similar to the prior method, the solvent solubilizes the surfaces of the bonding fibers, allowing them to flow and contact the pulp fibers and each other. Once the solvent is fully absorbed by the bonding fibers, the surfaces resolidify; forming a bonding matrix for the pulp fibers.

Although the preferred methods just described employ a hammermill to mix and defiberize the fibers, other attrition devices and defiberizers such as, for example, a pin mill or garnet roll can be employed equally as well. Mixing can also take place separate from the defiberization as in conduit 56.

The blend sheet 30 referred to in FIG. 1 and 52 referred to in FIG. 2 can be wet laid, for example, on a paper machine. As an example, a blend sheet of fifty percent (50%) bonding fibers and fifty percent (50%) fluff wood pulp can be formed on a paper machine, for example, at a basis weight of 150 grams per square meter (gsm). The amount and type of bonding fibers and pulp fibers can be varied greatly. For example, bonding fibers combined with a bicomponent thermoplastic fiber as a temporary bonding agent can be used to produce a blend sheet containing no pulp fibers. Temporary binders such as cooked starch can also be used at higher bonding fiber contents to provide sufficient integrity to the blend sheet during processing.

A bonded web can also be wet laid. A cellulose acetate/ pulp blend is first formed on a paper machine. Triacetin can be sprayed on the underside of the web as it leaves the paper machine. The web can then enter a honeycomb dryer, for example. The triacetin is drawn through the web in the dryer, thoroughly distributing the triacetin, and thus causing a stronger web to be formed.

During web formation in accordance with the preferred method, the rate of bonding development can be controlled by varying blend sheet temperature, the amount and type of finish on the bonding fibers, the hydrophobicity or hydrophilicity of the bonding fibers, the order and timing of when the materials are added in the web formation process, the distance ahead of the hammermill at which the solvent is applied, the feed rate of the blend sheet, the amount and type of solvent applied, the temperature of solvent when it is applied, and the size of the solvent droplets when they are applied (if the solvent is sprayed directly onto the web). The bonding medium may also be preplasticized to increase the rate of bonding development. After the web is formed, the rate of bond development is controlled by the temperature of the formed web (the higher the temperature, the quicker the solvent is absorbed by the polymeric material) and the density of the formed web. Hot or cold embossing the formed web will also produce immediate bonding in addition to enhancing and increasing the number of bonds.

In the preferred methods set forth above, the bonding medium and solvents are added at specific points in the process. One of ordinary skill will readily understand that the bonding medium and solvent can be combined at various times and locations in the manufacturing process and/or in the formation of absorbent articles, so long as the bonding medium, solvent, and fibers are in intimate contact when bonding is to occur. For example, as depicted in FIG. 1, cellulose acetate fibers can be admixed with wet pulp at the wet end of the paper machine that forms the blend sheet. Solvent can then be combined with the pulp before, during or after it is fiberized, for example in the hammermill, conduit 40 or on wire 44. Similarly, the cellulose acetate or other bonding medium can be added at any stage of the production process before the desired bonding is to take place.

Additives such as superabsorbent polymer can be fed into the air lay system after the hammermill at a point where good mixing occurs between the solvent-treated bonding medium and the superabsorbent polymer. Similar to the bond between cellulosic fibers and the solvent treated bonding medium, a weak capillary bond forms between the solvent-treated bonding medium and the superabsorbent polymer sufficient to retain the superabsorbent polymer in the web matrix during air laying. As the solvent is absorbed by the bonding medium over time, a strong solid bond between the superabsorbent material and the bonding medium will develop.

A variety of suitable constructs can be produced from cellulose webs formed in accordance with the present invention. The most common are absorptive consumer products such as diapers, feminine hygiene products such as feminine napkins, and adult incontinence products. For example, referring to FIG. 3, an absorbent article 10 comprises an acquisition layer 12 and an underlying storage layer 14. A liquid pervious facing sheet 16 overlies the acquisition layer 12. Throughout this description, layer 12 is referred to as an acquisition layer, it should be understood that the acquisition layer 12 can also serve as a distribution layer, i.e., distributing fluid from the location of insult. A liquid impervious back sheet 18 underlies the storage layer 14. If desired, the acquisition layer 12 can contain a strengthened layer of cellulosic fibers formed in accordance with the present invention, for example, by partially solubilizing cellulose acetate with triacetin. The cellulosic fibers may be crosslinked fibers. The strengthened web will provide a strong acquisition layer 12 for use in, for example, diapers. The bonding in the acquisition layer will help maintain its capillary structure, thus aiding fluid transport in multiple wettings. The storage layer 14 can similarly contain a strengthened web of cellulose fibers formed in accordance with the present invention. In the storage layer 14, however, additives such as superabsorbent polymers can also be incorporated to significantly increase the absorbent capacity of the storage layer 14. The superabsorbent polymer is distributed throughout the storage layer 14 and can attach to the bonding medium during the formation of the web. Thus the superabsorbent polymer remains distributed throughout the storage layer 14 during handling, and cannot fall to the bottom of or migrate through the storage layer 14 and thus lose its effectiveness.

Figure 3:
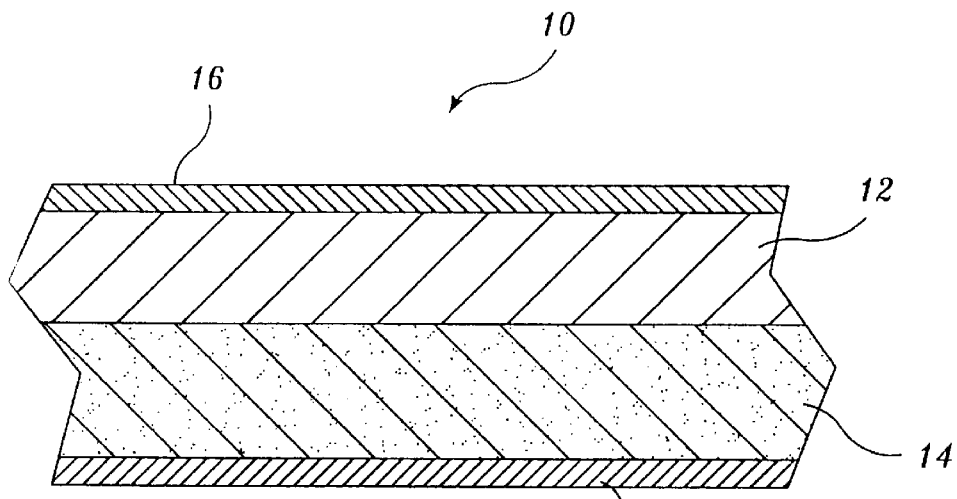
FIG. 3 is a schematic view of one absorbent product incorporating the strengthened web produced in accordance with the present invention.

The article of FIG. 3 can be assembled so that the acquisition layer 12 is brought into contact with the storage layer 14 while the bonding medium in the latter is still active, that is, partially solubilized. This will allow the storage layer to bond to at least the lower surface of the acquisition layer 12. Using the present invention in this manner eliminates the need to use hot melt glues to bond adjacent layers.

A stronger bond between the acquisition and storage layers can be achieved by incorporating some bonding medium in the acquisition layer in a location which allows it to bond with the bonding medium in the storage layer. Laying the storage layer 14 on the back sheet 18 while the bonding medium is still active may also bond the layer 14 to the back sheet 18. Similarly, the acquisition layer 12 may be bonded to the facing sheet 16 by laying the facing sheet on the acquisition layer 12 while the bonding medium therein is still active. Interbonding between layers can facilitate fluid transport across the layer interface.

The acquisition layer 12 may also be formed from cellulosic fibers, crosslinked or non-crosslinked, which are not bonded in accordance with the present invention. The acquisition layer may also be a nonwoven web of polyester, bicomponent or polypropylene fibers into which has been incorporated some of the bonding medium such as cellulose acetate fibers. In each of these constructions, including the construction in which the acquisition layer is formed in accordance with the present invention, the storage layer 14 will bond to the acquisition layer 12, aiding transport of liquid from the acquisition layer to the storage layer and also giving integrity to the entire construction.

Figure 4:
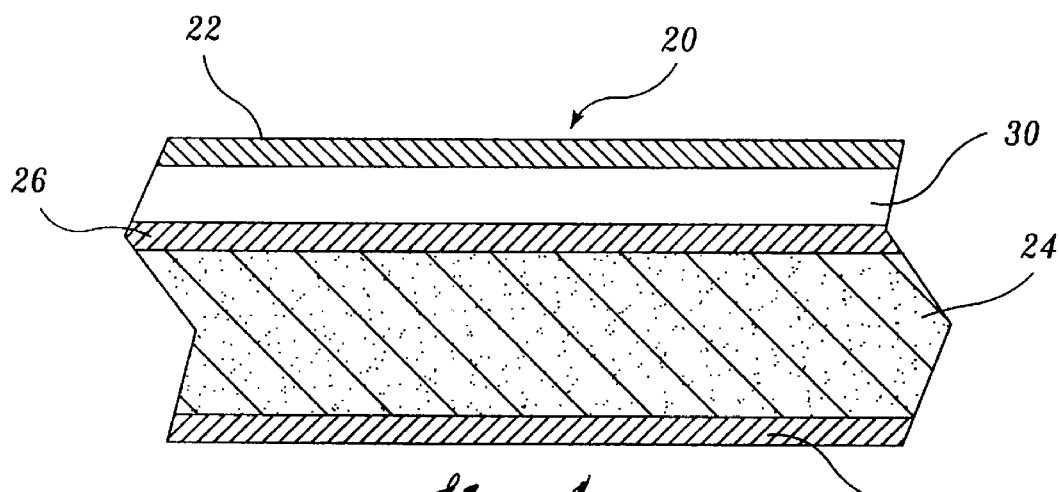
FIG. 4 is a schematic view of another absorbent product incorporating the strengthened web produced in accordance with the present invention.

The construct in FIG. 3 is shown for purposes of exemplifying a typical absorbent article, such as a diaper or feminine napkin. One of ordinary skill will be able to make a variety of different absorbent constructs using the concepts taught herein. For example, a typical construction for an adult incontinence absorbent structure is shown in FIG. 4. The article 20 comprises a facing sheet 22, a storage layer 24, formed of a strengthened cellulosic web made in accordance with the present invention, and a backing sheet 28. The facing sheet 22 is pervious to liquid while the backing sheet 28 is impervious to liquid. In this construct, the cellulosic web is formed on a liquid pervious tissue 26. The tissue 26 is composed of a polar, fibrous material. The bonding medium employed to make the storage layer 24 will cause the layer to adhere to the tissue 26 as well. If desired a wicking sheet or layer 30 can be interposed between the facing sheet 22 and the tissue 26 to speed distribution of liquid across the entire storage layer 24.

Figure 5:
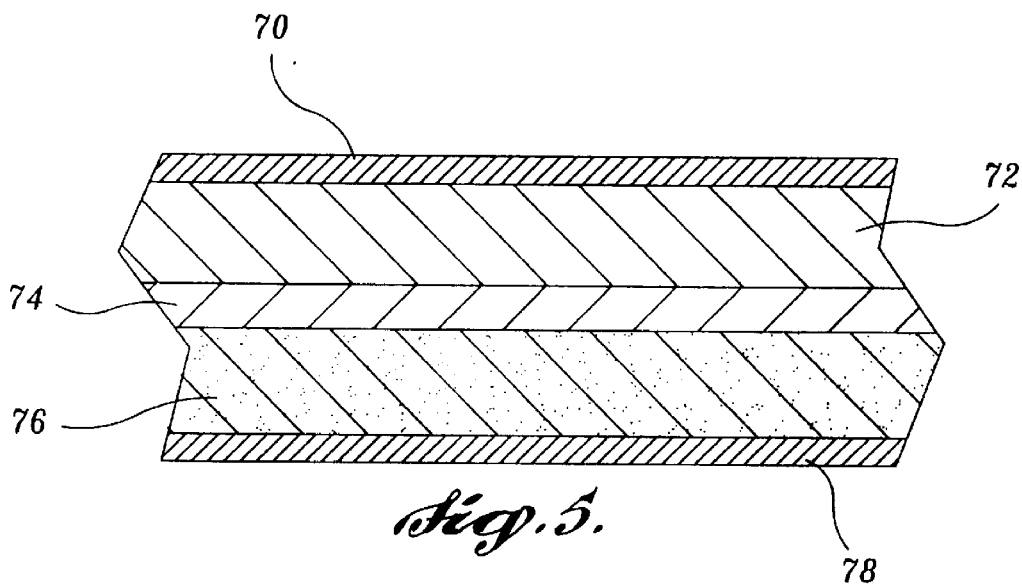
FIG. 5 is a schematic view of still another absorbent product incorporating the strengthened web produced in accordance with the present invention.

Referring to FIG. 5, another absorbent article includes a backing sheet 78, a storage layer 76, an intermediate layer 74 formed in accordance with the present invention, an overlying acquisition layer 72, and a facing sheet 70. The intermediate layer 74 contains, for example, cellulose acetate and triacetin, which are combined just prior to forming the article. The intermediate layer 74 thus can bond to both the acquisition layer 72 and the storage layer 76 to form an absorbent article with much more integrity than one in which the distribution and acquisition layers are not bonded to each other. The hydrophilicity of layer 74 can be adjusted in such a way as to create a hydrophilicity gradient among layers 72, 74 and 76. It should be understood that an independent intermediate layer is not required in order to get layer to layer bonding in accordance with the present invention. When one of two adjacent layers or both layers contain the bonding medium useful in the present invention, if the two layers are brought together when the bonding medium is still active, bonding between the two layers will occur and provide a stronger composite compared to if the bonding did not occur.

Other articles that can take advantage of the integrity increasing properties of the present invention include wipes, tissues, towels, and filters. Filters of glass fiber can also be strengthened using the bonding process of the present invention. It is also possible to produce a baling twine which may also be water dispersible. Articles formed by this invention can be used in those applications in which thermoplastic articles cannot be used, as for example, filtering hot oil.

EXAMPLES

The following examples are inserted to instruct one of ordinary skill how to make and use the invention. The examples are directed to various embodiments of the invention and are not intended in any way to limit the scope of Letters Patent granted hereon.

Experimental Procedures for Examples 1 and 2

The cellulose fibers used in the following examples are bleached southern pine Kraft fluff pulp available from the Weyerhaeuser Company and are referred to by the designation NB 416. The bleaching is elemental chlorine free. The fibers are bleached with chlorine dioxide. The cellulose acetate staple fiber used in the examples is either a 1.8 d.p.f, ¼" long, with coconut oil finish or 1.8 d.p.f, ⅛" long with a ST-90 mineral oil finish available from Hoechst Celanese. The cross-linked fluff pulp fiber is NHB 405, manufactured by Weyerhaeuser Co. The superabsorbent particles (SAP) are IM-3900 from Hoechst Celanese Co. The solvents used are industrial grade triacetin or dimethyl phthalate available from Aldrich Chemical Company.

On a first evening, pulp sheets of NB 416 were treated with solvent. In Example 1 five percent (5%) by weight of solvent based on the weight of the pulp was sprayed on one side of the sheet. Then the sheet was turned over, and five percent (5%) solvent by weight of the pulp was sprayed on the other side. In Example 2 varying amounts of solvent are used as indicated. The sheets were then stored overnight.

The next day, the solvent treated NB 416 pulp sheets were broken up by hand into small ½–¾" pieces and placed in a lab size Waring Blendor. To this, ⅛", 1.8 d.p.f., cellulose acetate staple fiber from Hoechst Celanese was added, except in the control. Superabsorbent particles were also added. The Waring Blendor was turned on low power for 5 seconds to defiber the pulp and mix the pulp and cellulose acetate fibers with each other and the particles. An additional advantage of the invention was noted during the fiberizing, namely, that the dust and fibers normally produced were greatly reduced by the presence of the solvent.

All absorbent pads were formed in the laboratory on a fabric sheet in a conventional 6" diameter circular laboratory pad former. The pad former was equipped with a pin mill fluffing device. The pulp mixture from the Waring Blendor was quantitatively transferred to a pan. From there, small clumps were individually fed into the pad former. Care was taken to insure that all the ingredients were fed into the pad former.

The formed pads were carefully removed from the pad former by removing the fabric on which the pads were formed and placed in a cold press. A Teflon block, with a cut-out 6" diameter hole was placed over the pad. A Teflon plug was placed over the pad and the pad was cold pressed to the desired pad density for 1.1–1.3 minutes.

The pads were then taken out of the cold press and 4 pads were stacked on top of one another. Sufficient weight was place on the 4 pads to collapse the pads down to a pre-determined caliper. Shims were used to support the applied weight and maintain the desired caliper. The pads were allowed to cure at room temperature, under this weight, for a period of at least 2 days. 4" by 4" test pads are then cut from each of the circular pads.

The aqueous solution used in the tests is a synthetic urine available from National Scientific under the trade name RICCA. It is a saline solution containing 135 meq/l sodium, 8.6 meq/l calcium, 7.7 meq/l magnesium, 1.95% urea by weight (based on total weight), plus other ingredients.

An absorptive capacity test is performed on a test pad by recording the initial sample dry weight ($W_1$) in grams. The test pad, is then placed on a wire support screen and immersed in synthetic urine in a horizontal position. If the pad contains superabsorbent particles, the pad is immersed for 30 minutes. If the pad does not contain any superabsorbent particles, the pads are immersed for 10 minutes. The pads are removed from the synthetic urine solution and allowed to drain for 5 minutes. The pads are then placed under a 1.0 psi load for 5 minutes. The wet pad is reweighed ($W_2$) in grams. The total capacity under load is reported as $W_2-W_1$. The unit capacity under load is calculated by dividing the total capacity by the dry weight, ($W_2-W_1/W_1$). If test pads contain a solvent, the weight of the solvent is not included in the dry weight.

A dry pad tensile integrity test is performed on a 4" by 4" square test pad by clamping a dry test pad along two opposing sides. About 3" of pad length is left visible between the clamps. The sample is pulled vertically in an Instron testing machine and the tensile strength measured is reported in N/m. The tensile strength is converted to tensile index, Nm/g by dividing the tensile strength by the basis weight $g/^2$.

A wet tensile integrity test is performed by taking the sample from the total capacity test and placing the sample in a horizontal jig. Opposing ends of the sample are clamped and pulled apart horizontally on the Instron testing machine. The wet tensile strength, N/m is converted to tensile index, Nm/g, by dividing by the sample basis weight, $g/m^2$.

Example 1

6" diameter pads with the following composition were made in the laboratory pad former. The percentage noted after the SAP weight is the percentage of SAP in the test pad based on the total weight of the pad.

| No. | Sample | Composition | Total Weight |
|---|---|---|---|
| 1 | Control | 6.05 g NB 416<br>3.95 g SAP (39.5%) | 10.0 g |
| 2 | Bonded<br>100% Fiber | 5.75 g NB 416<br>0.30 g cellulose<br>acetate<br>3.95 g SAP (39.5%) | 10.0 g |

-continued

| No. | Sample | Composition | Total Weight |
|---|---|---|---|
| 3 | Bonded<br>⅔ Fiber | 3.375 g NB 416<br>0.20 g cellulose<br>acetate<br>3.95 g SAP (52.5%) | 7.5 g |
| 4 | Bonded<br>½Fiber | 2.61 g NB 416<br>0.15 g cellulose<br>acetate<br>3.95 g SAP (59%) | 6.7 g |

After forming the pads with the above composition, and storing at a prescribed density for 3 days, 5 pads for each composition were tested with the following results:

| | Density | Tensile Index Nm/g | | Absorptive Capacity | |
|---|---|---|---|---|---|
| Sample # | g/cc | Dry | Wet | Total (g) | Unit (g/g) |
| 1 | 0.17 | 0.02 | 0 | 72.5 | 14.4 |
| 2 | 0.18 | 0.15 | 0.049 | 74.3 | 14.4 |
| 3 | 0.14 | 0.08 | 0.032 | 65.5 | 17.6 |
| 4 | 0.13 | 0.04 | * | 64.8 | 19.7 |

*Exhibited wet pad integrity but the sample was so swollen that it could not be tested with the clamping system.

Example 1 illustrates that superabsorbent particles, at a higher concentration than normally used in commercial diaper absorbent cores, can be incorporated in a fluff pulp pad bonded with this technology. The example also illustrates that the pads bonded with cellulose acetate staple fiber developed good wet and dry strength integrity, even though some of the pads were composed of more than 50% superabsorbent particles. This example also illustrates that even with removal of more than 50% of the fiber compared with the control, the total pad capacity under load decreased only by about 10%. While the total pad absorptive capacity under load decreased, the unit absorptive capacity increased. Electron micrographs indicate the superabsorbent particles are well attached to cellulose acetate fibers which in turn are strongly attached to other pulp or cellulose acetate fibers in the pad.

Example 2

This example illustrates that dimethyl phthalate can be used to activate bonding in place of triacetin.

As in Example 1, fluff pulp sheets of NB 416 were treated with 5, 15 and 30% by weight triacetin, based on the weight of the pulp. Additional pulp sheets were treated with 5, 15 and 30% by weight dimethyl phthalate, based on the weight of the pulp. The pulp sheets were defibered in the Waring Blendor and then 10% by weight cellulose acetate, based on the weight of pulp added to the blender.

The following pulp blends were made:

| Sample # | Triacetin level % | Dimethyl Phthlate level % | Cellulose Acetate level % |
|---|---|---|---|
| 1 (Control) | 0 | 0 | 0 |
| 2 | 15 | 0 | 0 |
| 3 | 0 | 15 | 0 |
| 4 | 5 | 0 | 10 |
| 5 | 15 | 0 | 10 |
| 6 | 30 | 0 | 10 |

| Sample # | Triacetin level % | Dimethyl Phthlate level % | Cellulose Acetate level % |
|---|---|---|---|
| 7 | 0 | 5 | 10 |
| 8 | 0 | 15 | 10 |
| 9 | 0 | 30 | 10 |

The pads were tested for wet and dry tensile strength with the following results:

| | Tensile Index, Nm/g | |
|---|---|---|
| Sample # | Dry | Wet |
| 1 | 0.11 | 0.056 |
| 2 | 0.05 | 0.039 |
| 3 | 0.05 | 0.042 |
| 4 | 0.04 | 0.042 |
| 5 | 0.44 | 0.180 |
| 6 | 0.14 | 0.23 |
| 7 | 0.36 | 0.15 |
| 8 | 0.44 | 0.166 |
| 9 | 0.37 | 0.132 |

Example 3

This example illustrates that an unsoftened version of NHB 405 cross-linked fluff pulp fiber (manufactured by Weyerhaeuser) that has been air laid can be bonded into structures having superior wet and dry pad tensile strength. This example also illustrates that changing the cellulose acetate staple length from 1/8"41 to 1/4" improved the wet tensile strength compared to the control sample that contained cellulose acetate fiber that was not activated by a solvent. The cross-linked fiber was not treated as in Example 1 because it was not in sheet form. The cross-linked fiber was first treated separately in a mini-blender with various levels of cellulose acetate. Then various levels of triacetin were sprayed in the blender while the blender was in motion.

The following pad compositions were made in the 6" pad former as in Example 1:

| Sample # | Triacetin level % | Cellulose Acetate 1/4" (%) | Cellulose Acetate 1/8" (%) |
|---|---|---|---|
| 1 | 0 | 10 | 0 |
| 2 | 5 | 2.5 | 0 |
| 3 | 5 | 5 | 0 |
| 4 | 0 | 0 | 10 |
| 5 | 5 | 0 | 2.5 |
| 6 | 5 | 0 | 5 |

The pads were cold pressed and stored for 2 days under pressure so that the final pad density was about 0.09 g/cc. After 2 days, 4" by 4" test samples were treated for wet and dry tensile strength.

| | Tensile Index, Nm/g | |
|---|---|---|
| Sample # | Dry | Wet |
| 1 | 0.026 | 0.034 |
| 2 | 0.073 | 0.065 |
| 3 | 0.166 | 0.100 |

| | Tensile Index, Nm/g | |
|---|---|---|
| Sample # | Dry | Wet |
| 4 | 0.020 | 0.024 |
| 5 | 0.078 | 0.033 |
| 6 | 0.114 | 0.035 |

Example 4

This example illustrates that the cellulose acetate fiber can be incorporated into one pulp sheet and the cellulose acetate plasticizer can be incorporated into another separate pulp sheet. When both sheets are fed into a hammermill simultaneously and air laid into a web, bonding resulted.

Experimental Procedure

20% by weight of cellulose acetate staple fiber, 1.8 d.p.f, 1/8" ST-90 finish from Hoechst Celanese (based on the dry weight of the combined pulp and cellulose acetate) was slurried in water with NB 416 pulp. The pulp slurry was then wet laid on a Noble & Wood pilot paper machine into a sheet, target basis weight 300 g/m² and dried to about a 6% moisture content.

For the solvent treated rolls, a roll of NB 416 pulp, basis weight 750 g/m², 6% moisture content was unwound and triacetin was sprayed, at 20% by weight based on the weight of the pulp, on one side. After spraying, the pulp sheet was immediately rewound.

Two rolls of the above formed cellulose acetate/NB 416 pulp blend sheet and one roll of the above formed triacetin treated NB 416 pulp were introduced into the hammermill.

All sheets were fed simultaneously into the hammermill. The hammermill defibers the pulp sheets into individual fibers.

From the hammermill, the defibered pulp was transported to the head of a DanWeb air lay machine. A target basis weight was 300 gm². The web samples were cold calendered immediately at a 40 psi setting. After sitting one hour, the web samples were passed through the web calender again at the same setting. The final web density was about 0.090 g/cc. The composition of the final web was approximately 11% triacetin and 9% cellulose acetate, based on the dry weight of the pulp fiber. The web samples were allowed to cure for 2 days at room temperature and the wet and dry tensile strength were measured as in Example 1.

| Sample | Density g/cc | Tensile Index, Nm/g | |
|---|---|---|---|
| | | Dry | Wet |
| Control | 0.089 | 0.058 | 0.053 |
| Cellulose acetate bonded web | 0.098 | 0.233 | 0.176 |

Example 5

This example illustrates that high concentrations of superabsorbent particles can be incorporated into a air laid bonded web.

Experimental Procedure

To the air laid web produced as in Example 4, SAP (Hoechst Celanese IM 3900) at 450 g/m² was added with a spray nozzle, at the forming head of the Danweb air lay machine.

Results

A sodium analysis showed that the bonded web was composed of 62% superabsorbent polymer and 38% pulp fiber and cellulose acetate. The superabsorbent polymer was well bonded, as shown by electron micrographs and did not readily fall out of the web. A similar control pulp with the same amount of superabsorbent particles but no bonding fibers exhibited poor pad integrity and the superabsorbent particles readily fell out of the pad. The cellulose acetate bonded web held together when the web was placed in synthetic urine for 30 minutes and the superabsorbent particles became swollen. The similar control pad completely disintegrated.

The following dry tensile strength and absorptive capacity under load were measured as in Example 1.

| Sample | Tensile Index, Nm/g | Absorptive Capacity, g/g |
| --- | --- | --- |
| Control | 0.091 | 20.46 |
| Cellulose acetate bonded web | 0.123 | 20.71 |

Example 6

This example illustrates the impact of the level of solvent on the development of strength when the cellulose acetate staple fiber is kept constant. The strength goes through an optimum. It is theorized that at low amounts of solvent, the cellulose acetate forms fewer bonds with a smaller bond surface area. As more solvent is added, the number and surface area of the bonds increase and the web becomes stronger. At even higher levels of solvent, the cellulose acetate fiber becomes weaker and the web strength decreases.

Experimental Procedure

One batch of a defibered unsoftened version of NHB 405 cross-linked pulp fiber (manufactured by the Weyerhaeuser Company) and one batch of defibered NB 416 (bleached pulp fiber) were each blended with 10% by weight cellulose acetate (1.8 d.p.f, ¼" coconut oil finish from Hoechst Celanese) in a blender.

The unsoftened NHB 405/cellulose acetate blend was split into 4 parts. One part was kept as a control, the 3 parts were sprayed with 10%, 20% and 30% triacetin, respectively, based on the pulp weight, while being agitated in the blender. The NB 416/cellulose acetate blend was also split into 4 parts. One part was kept as a control and the other 3 parts were respectively sprayed with 5, 15 and 30% triacetin, based on the weight of the pulp.

The following results were obtained:

| Fiber | Triacetin level % | Density g/c | Tensile Index, Nm/g Dry | Tensile Index, Nm/g Wet |
| --- | --- | --- | --- | --- |
| unsoftened NHB 405/cellulose acetate | 0 | 0.064 | 0.026 | 0.034 |
| unsoftened NHB 405/cellulose acetate | 10 | 0.080 | 0.199 | 0.137 |
| unsoftened NHB 405/cellulose acetate | 20 | 0.082 | 0.176 | 0.254 |
| unsoftened NHB 405/cellulose acetate | 30 | 0.085 | 0.125 | 0.205 |
| NB 416/cellulose acetate | 0 | 0.114 | 0.052 | 0.069 |
| NB 416/cellulose acetate | 5 | 0.123 | 0.385 | 0.182 |
| NB 416/cellulose acetate | 15 | 0.121 | 0.561 | 0.519 |
| NB 416/cellulose acetate | 30 | 0.136 | 0.354 | 0.361 |

Example 7

This example illustrates that is possible to develop bonding with other types of fibers that are softened or solubilized by a solvent.

In this example, vinyl acetate copolymer fibers (MP-Faser, 3.3 dtex/1.25 mm fibers from Wacker Chemicals (U.S.A.) Inc.) were blended, 20% by weight based on the weight of the pulp, with some defibered unsoftened NHB 405 cross-linked pulp fibers. The NHB 405 had previously been treated with triacetin, 30% by weight. The two fibers were blended together in a laboratory Waring Blendors at low speed for 30 seconds. The blended mixture was then slowly fed into the pad former as in Example 1 to produce a uniform 6" diameter pad of about a 500 g/m$^2$. The pad was subsequently cold pressed on a Wabash lab press for 1 min and 30 seconds to produce a pad of 0.1 g/cc. The pad was then stored under a 3 lb. plate. Noticeable bonding developed in the pad when pad was checked again in 24 hours.

Example 8

This example illustrates that very little triacetin is necessary to activate bonding when the triacetin can be directed to the cellulose acetate fibers.

A wet laid blend sheet of pulp and cellulose acetate having a 150 g/m$^2$ basis weight was made on a Noble and Wood pilot paper machine. The sheet was composed of 75 g/m$^2$ of cellulose acetate staple fiber, 1.8 d.p.f, ¼", coconut finish and 75 g/m$^2$ of lightly refined NB 416 fluff pulp.

Two rolls of NB 416 pulp having a 750 g/m$^2$ basis weight were mounted on stands and a tail from each roll was fed into a hammermill. The blend sheet, containing 50% cellulose acetate staple fiber was mounted on a stand placed between the two NB 416 rolls and a tail was fed into the hammermill between the two sheets of NB 416 pulp. Triacetin, 17.2% by weight based on the weight of the blend sheet, was evenly sprayed on only the cellulose acetate blend sheet on one side, between the hammermill and the mounting stand. Because the blend sheet was only 150 gsm, the triacetin quickly penetrated through the sheet. In the hammermill, the three sheets were defibered and mixed together. From the hammermill, the mixed defibered pulp was transported to the forming head of a Danweb air lay machine, where it was air laid into a web.

Within 30 to 60 minutes after the web was formed, obvious bonding occurred in the pulp sheet. The final bonded air lay web had a composition of 1.6% triacetin, 4.5% cellulose acetate and 93.9% NB 416 fluff pulp.

Example 9

This example illustrates that a pulp/cellulose acetate pad does bond to other substrates that are in contact with the pad while bonding is developing. This is important because it is often important to have the absorbent core in intimate contact with tissue and nonwoven coverstocks also used in absorbent products.

Several air laid webs, 180 g/m² basis weight were made on a Danweb air lay machine. The webs were composed of an unsoftened NHB 405 cross-linked pulp blended with 10% by weight, based on the pulp of cellulose acetate fiber (Hoechst Celanese ⅛", 1.8 d.p.f., CS-90 finish). Triacetin (8% by weight based on the pulp fiber) was sprayed onto the pulp blend at the transport fan of the Danweb.

After manufacture, the air laid web was cut into rectangular 18"×14" pieces,. The pieces were stacked in two piles 200 high with a latex bonded nonwoven sheet between each sample. A piece of corrugated cardboard was placed over both sample piles. A uniform weight, 252 lb. or 0.5 psi, was placed over the piles and the samples were allowed to develop pad bonding at room temperature over a period of 5 days.

When the weight was removed, the top air laid web from each pile was well bonded to the corrugated cardboard surface that was in direct contact with the air laid web.

Example 10

Variations of the hydrophilicity/hydrophobicity of the solvent soluble bonding medium can be used to advantage in absorbent products. This example illustrates that it is possible to make a low density bonded pad that wicks and wets well but does not require any surfactant. In normal processing of cellulose acetate fibers, oils are added to the cellulose acetate to lubricate the fibers. This reduces fiber to fiber and fiber to metal friction and this in turn reduces fiber breakage. Because of this, cellulose acetate is hydrophobic until its surface becomes wet. Thereafter, the surface acts like a hydrophilic surface.

Hydrophobicity of the air laid pads was noted when using cellulose acetate fibers having a mineral oil or coconut oil finish. The hydrophobicity was particularly pronounced when the blending time was extended, when the triacetin level was increased, or when the curing temperature was raised.

In this example, cellulose acetate fibers (Hoechst Celanese 1¼" length, 3.0 d.p.f) manufactured with a water lubricant, were cut into smaller fibers of approximately ¼" with scissors. The cellulose acetate fibers were then blended, 10% by weight based on the pulp, with a NB 416 pulp that had previously been treated with 15% by weight triacetin based on the pulp. The fluffed pulp/cellulose acetate blend was then made into a 10 g pad on the 6" pad former as in Example 1. The pad was then compressed to a density of about 0.1 g/cc. A portion of the pad was separated and allowed to cure in an oven at 105 degrees C. for 3 days. The remainder of the pad was allowed to develop bonding under a slight pressure (0.3–0.4 psi) for 3 days.

Both the oven cured and room temperature cured samples developed good pad integrity. The samples exhibited hydrophilic properties. A water drop test immediately wet both samples and wicked liquid away from the point of impact. No hydrophobicity from the cellulose acetate fiber was apparent. By varying the finish on the cellulose acetate and by varying the amount of cellulose acetate employed, the hydrophobic/hydrophilic nature of the product can be altered at will.

Example 11

This example illustrates that while room temperature is sufficient to develop bonding, increases in temperature during bonding is beneficial in developing a stronger level of bonding more rapidly.

Unsoftened NHB 405 cross-linked pulp was treated with 10% triacetin, by weight based on the pulp, in a Waring Blendor. Cellulose acetate (Hoechst Celanese, ¼", 1.8 d.p.f.) coconut oil finish, was blended with the solvent treated cross-linked pulp so that the final compositions contained 10% by weight cellulose acetate fiber.

The mixture was made into 6" pads with the laboratory pad former having a basis weight of about 55 g/m². The pads were cold pressed to a density of approximately 0.1 g/cc. One set of pads was allowed to cure, at a constant caliper for 90 hours. One hour after manufacture, another set of pads was placed in an oven at 50° C. for 90 hours. The caliper was also maintained constant. One hour after manufacture, a third set of pads was placed in a 100° C. oven for 90 hours at constant caliper.

Pads were removed from each set after one hour, four hours, 20 hours and 90 hours and the dry tensile strength was measured.

| Temperature | Tensile Strength, N/m | | | |
|---|---|---|---|---|
|  | 1 hour | 4 hours | 20 hours | 90 hours |
| 20° C. | 24 | 24 | 208 | 243 |
| 50° C. | 235 | 289 | 353 | 422 |
| 100° C. | 410 | 548 | 667 | 739 |

The results show that by elevating the temperature 30°, the tensile strength is almost equal to the tensile strength developed at 20° C. after 90 hours. At 100° C., the tensile strength greatly exceeds the tensile strength attained at room temperature in 90 hours. After 90 hours, the sample cured at 100° C. is nearly three times as strong as the sample cured at room temperature.

Example 12

This example shows that the capacity for absorbing synthetic urine is not adversely affected by bonding the cellulosic fibers in a web in accordance with the present invention.

Six-inch round test pads were created in a conventional manner using NB 416 pulp and cellulose acetate fibers (¼", 1.8 d.p.f). A blend of 10% by weight cellulose acetate and 90% by weight NB 416 pulp was used. After the fibers were blended, 10% by weight triacetin based on the weight of the pulp was added. Superabsorbent polymer (SAP) was also added. Test pads containing 50% by weight, 60% by weight, and 70% by weight superabsorbent polymer based on the weight of the pulp were prepared. Control pads containing 50%, 60%, and 70% by weight SAP were also prepared, omitting the solvent and the cellulose acetate.

The pads were then tested for absorption capacities by immersing them in synthetic urine for 30 minutes. The pads were then allowed to drain. The pads were then weighed and inserted in a centrifuge for 75 seconds. The pads were again weighed to determine their dry weight. Absorption capacities in a gram of urine absorbed per gram of dry weight of pad basis were then calculated. The results are set forth in the following table.

| SAP CONTENT | 50% Total Capacity (g) | g/g | 60% Total Capacity (g) | g/g | 70% Total Capacity (g) | g/g |
|---|---|---|---|---|---|---|
| Control | 89 | 10.6 | 149 | 14.2 | 249 | 17.7 |
| Bonded | 95 | 10.5 | 150 | 13.6 | 247 | 16.9 |

The results show that bonding slightly reduced the gram per gram absorption capacity, but that total pad capacity stays about the same with varying loadings of SAP.

Example 13

The purpose of this example is to illustrate that the order of addition of the solvent and bonding medium to the pulp significantly alters the strength development and hydrophobicity of the resulting pad. Combining the solvent with the cellulose fiber and thereafter blending with bonding fibers yielded a relatively strong and hydrophilic bonded web. First blending the bonding fibers and then adding the triacetin yielded a bonded web with lower strength and that was relatively hydrophobic.

Six-inch test pads containing 10% cellulose acetate (¼" length, 1.8 d.p.f.) and 90% cellulosic fibers (unsoftened version of NHB 405) were prepared in a conventional manner. A first sample A was formed by first adding 10% by weight based on the pulp weight triacetin to the pulp. Ten percent cellulose acetate (based on the combined weight of the pulp and cellulose acetate) was then added and the resulting mixture blended. Sample B was formed by first adding the cellulose acetate (10% be weight) to the pulp (90% by weight) and blending that combination, and thereafter adding triacetin and again blending the combination. Both sample pads contained 10% by weight triacetin based on the weight of the pulp. Wet and dry tensile integrity tests were then performed and a tensile index and tensile energy absorption were calculated. Tensile energy absorption is the area under the curve of tensile strength versus stretch before breaking. Hydrophobicity was tested by placing a sample on the surface of synthetic urine. Its float time was then measured. A long float time indicates that the pad is hydrophobic. The results are set forth below.

| Order of Addition | Strength Dry | | Wet | | Float time |
|---|---|---|---|---|---|
| | TI (Nm/g) | TEA (J/m²) | TI (Nm/g) | TEA (J/m²) | (sec) |
| A | 0.48 | 67 | 0.25 | 36 | 0–1 |
| B | 0.36 | 54 | 0.21 | 33 | 17 |

It is observed that the lower strength of pad B is probably caused by poor triacetin distribution. Moreover the hydrophobicity of pad B is probably caused by smearing of dissolved cellulose acetate over the pulp fiber surfaces during manufacture of the pad.

Example 14

The purpose of this example is to illustrate that crimped cellulose acetate fibers provided a lower strength pad than straight fibers when otherwise processed in accordance with the present invention.

NB 416 pulp was first treated with 10% by weight triacetin based on the weight of the pulp. It was then combined with cellulose acetate in the ration of 90% by weight pulp to 10% by weight cellulose acetate (¼" length). Several six-inch test pads were produced in a conventional manner using cellulose acetate having no crimp (2.0 d.p.f), a slight crimp (1.8 d.p.f, 4–6 crimps per inch) and a high crimp (1.8 d.p.f, 22–24 crimps per inch). Wet and dry tensile integrity tests were then conducted and the tensile index and tensile energy absorption calculated. The results are set forth below:

| Cellulose acetate crimp | | None | Slight (4–6) | High (22–24) |
|---|---|---|---|---|
| Dry | TI (Nm/g) | 0.74 | 0.48 | 0.37 |
| | TEA (J/m²) | 106 | 67 | 61 |
| Wet | TI (Nm/g) | 0.52 | 0.25 | 0.18 |
| | TEA (J/m²) | 71 | 36 | 38 |

The results illustrate that when crimped cellulose acetate was employed, the strength of the pad is dramatically decreased. It is believed this is due to a reduction in the number of contact points between the cellulose acetate fiber and the cellulosic fibers.

Example 15

The purpose of this example is to illustrate that the strength of a pad formed in accordance with the present invention increased with the length of the cellulose acetate fibers employed.

Six-inch pads were formed in accordance with the present invention. NB 416 pulp fibers were first treated with 10% by weight triacetin based on the weight of the pulp fibers. The pulp was then combined with cellulose acetate to form a web containing 90% by weight pulp and 10% by weight cellulose acetate. Several samples were formed using 3.75 d.p.f cellulose acetate fibers with lengths ranging from ⅛" to ½". Wet and dry strength tensile integrity tests were then performed and the tensile index and tensile energy absorption calculated. The results are set forth in the table below.

| | | ⅛" | ¼" | ⅜" | ½" |
|---|---|---|---|---|---|
| Dry | TI | 0.21 | 0.32 | 0.34 | 0.42 |
| | TEA | 30 | 45 | 64 | 80 |
| Wet | TI | 0.10 | 0.22 | 0.29 | 0.36 |
| | TEA | 17 | 34 | 50 | 63 |
| % Wet/Dry | TI | 48% | 69% | 85% | 86% |
| Strength | TEA | 57% | 76% | 78% | 79% |

The test results clearly indicate that the strength of a web increased with the length of the cellulose acetate fibers.

Example 16

The purpose of this example is to illustrate that pretreating superabsorbent polymer prior to adding it to an absorbent pad resulted in greater pad strength.

The pulp used in this example is an unsoftened and bleached version of NHB 405. Cellulose acetate employed was ¼" long and 1.8 d.p.f. A 6" control test pad was first formed comprising 60% by weight untreated pulp and 40% by weight SAP to which had been added, 2% by weight triacetin based on the weight of the SAP. A second 6" test pad was then produced by first adding 10% by weight (based on the weight of the pulp) triacetin to the pulp. The pulp was then blended with cellulose acetate in a 90/10 weight ratio. Untreated SAP was also added to bring the final weight ratio to 40% SAP and 60% combined pulp and cellulose acetate.

A final 6" test pad was prepared as just described with the exception that the SAP was first treated with 2% by weight triacetin based on the weight of the SAP. A dry pad tensile integrity test was then performed and the tensile index and tensile energy absorption calculated. The results are set forth in the table below.

|  | Strength TI | (Dry) TEA |
|---|---|---|
| Pulp untreated SAP treated | 0.04 | 4 |
| Pulp treated (10% TA) SAP untreated | 0.24 | 18 |
| Pulp treated SAP treated | 0.33 | 29 |

The SAP was still flowable after being pretreated with triacetin. In addition it was observed that the SAP retention was improved when pretreated with triacetin and formed into a pad in accordance with the present invention. Finally, pad strength was similarly improved as shown by the foregoing data.

Example 17

The purpose of this example is to illustrate that triethyl citrate (TEC) is an excellent solvent for use in accordance with the present invention. In addition, retention time for triethyl citrate in a cellulose fiber matrix when stored in the open is much longer than for triacetin in a fiber matrix. In addition, triethyl citrate causes a stronger bond to be formed between the bonding medium and the cellulose fibers.

Six-inch test pads were formed in a conventional matter. Ten percent solvent was first applied to the cellulose fibers based on the weight of the fibers. The cellulose fibers were then combined with cellulose acetate in a 90/10 weight proportion. A first set of test samples were then stored in plastic bags and in an open room under normal relative humidity conditions. A second set of test samples were periodically selected from the bags and from the open room for dry pad tensile integrity tests. The results of those tests are set forth in the table below.

| Storage Time | Bagged Strength (Dry) (Nm/g) | | Open Room | |
|---|---|---|---|---|
| (Hours) | TA | TEC | TA | TEC |
| 0 | 0.63 | 0.87 | | |
| 25 | | | 0.63 | |
| 75 | 0.65 | 0.91 | 0.61 | 0.88 |
| 175 | 0.62 | 0.90 | 0.51 | 0.89 |
| 725 | 0.62 | 0.88 | 0.34 | 0.89 |

These results clearly indicate that the dry tensile strength of the pad formed with triethyl citrate changed very little over time and was virtually independent of whether the pad was stored in a bag or in the open room. Conversely, the strength significantly decreased when the pad was stored in the open room. The results indicate that the triacetin dissipated to the atmosphere. The strength of the pad produced with triacetin when stored in a bag did not vary over time.

Example 18

The purpose of this example is to illustrate the effect of densification of a pad produced in accordance with the present invention when compared with a control pad. A control pad was produced using only NB 416 pulp. A second pad was produced in accordance with the present invention by first treating NB 416 pulp with 10% by weight triacetin based on the weight of the pulp. The pad was then formed using a 90/10 weight blend of the treated pulp and cellulose acetate. The plurality of test pads were then calendered to varying densities. Tensile integrity tests were then conducted on the pad and the tensile energy absorption (TEA) calculated. The pads that were calendered to a density on the order of 0.4 g/cc exhibited a tensile energy absorption of 7 and 9 J/m$^2$ for the control and bonded pads, respectively. A control pad that was densified on the order of 0.19 g/cc exhibited a TEA of approximately 15 J/m$^2$. Conversely, a bonded pad that was densified to on the order of 0.22 g/cc exhibited a TEA on the order of 50 J/m$^2$. Finally, a control pad that was densified to on the order of 0.275 g/cc exhibited a TEA of approximately 18 J/m$^2$, while a bonded pad densified to on the order of 0.29 g/cc exhibited a TEA of on the order of 110 J/m$^2$. These results indicate that the strength of a non-bonded pad will increase slightly with densification while the strength of a bonded pad will increase significantly with densification.

Micrographs

Figure 6:
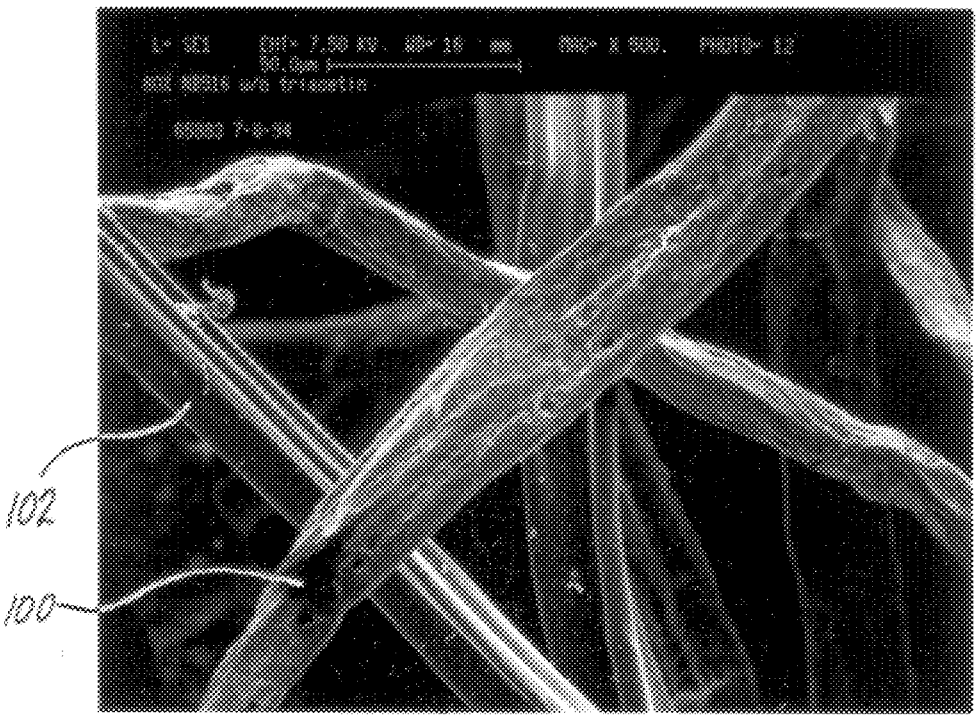
FIG. 6 is a photomicrograph of cellulose acetate fibers and cellulose pulp fibers without bonding.

To better illustrate the mechanism of the present invention, refer to the appended micrographs. In FIG. 6 a cellulose fiber 100 is shown adjacent a cellulose acetate fiber 102 before a solvent is added to the web. Both fibers are relatively free to move.

Figure 7:
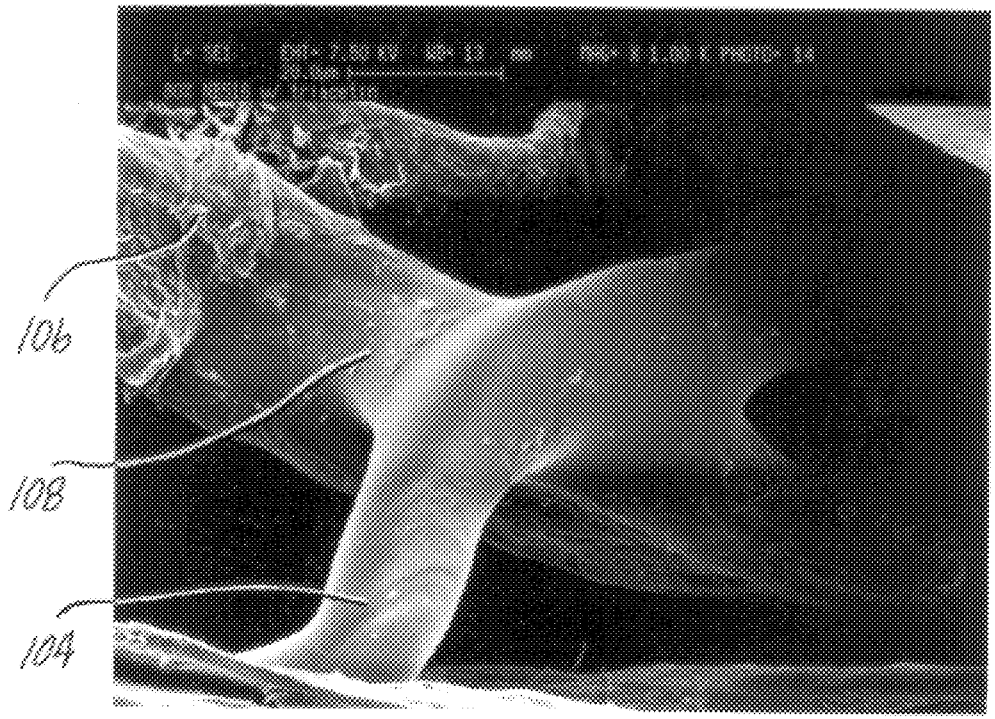
FIG. 7 is a photomicrograph showing cellulose acetate fibers bonded to cellulose pulp fibers.
Figure 8:
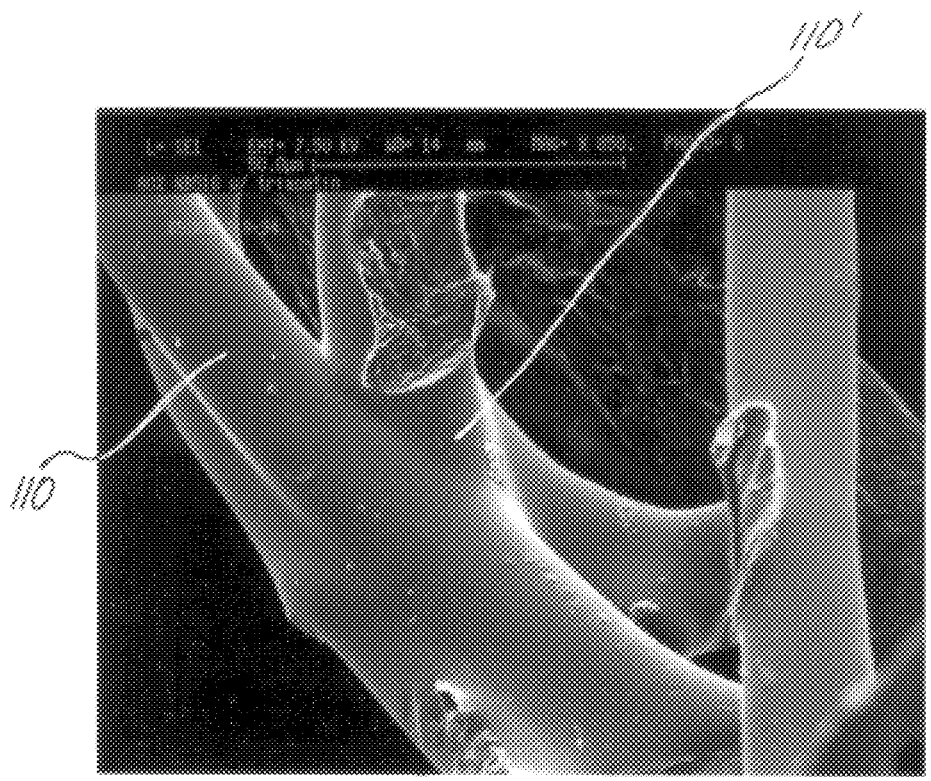
FIG. 8 is a photomicrograph showing cellulose acetate fibers bonded to themselves.

In FIG. 7, after a solvent has been added to the system, the surface of cellulose acetate fiber 104 is partially solubilized and flows onto the surface of a cellulose fiber 106 in the region 108. The cellulose acetate has wetted the cellulose fiber in region 108 and firmly adheres to it after the triacetin is absorbed. In FIG. 8 two cellulose acetate fibers 110 and 110' are shown after triacetin has been added to the web. The surfaces of the fibers have been partially solubilized and have flowed into each other. Again, after the triacetin is absorbed, the cellulose acetate resolidifies and causes the fibers to adhere to each other.

Figure 9:
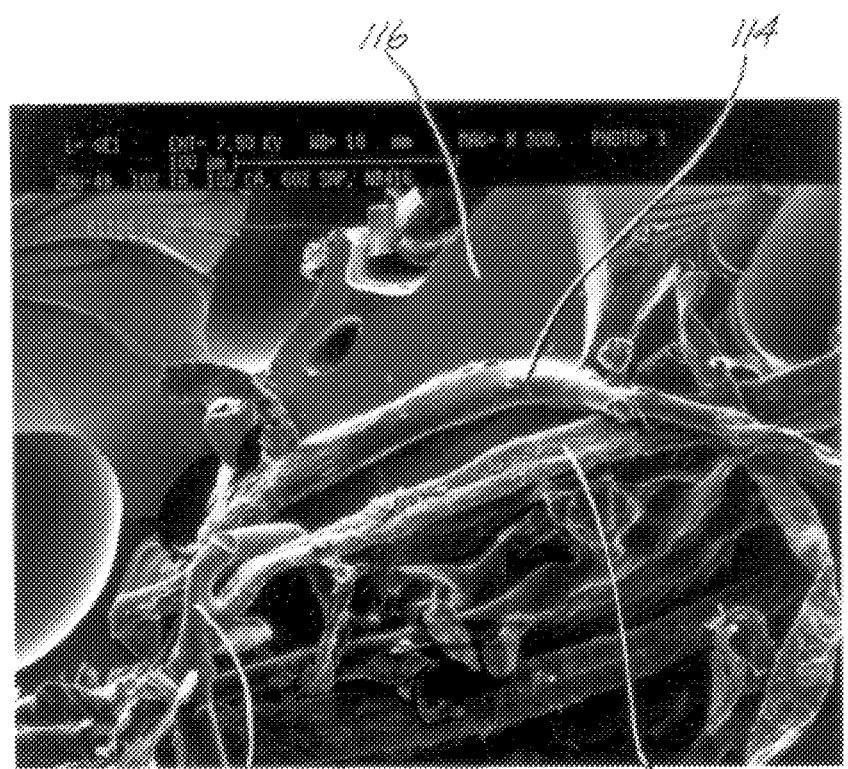
FIG. 9 is a photomicrograph showing cellulose acetate fibers bonded to cellulose pulp fibers and to superabsorbent particles.
Figure 10:
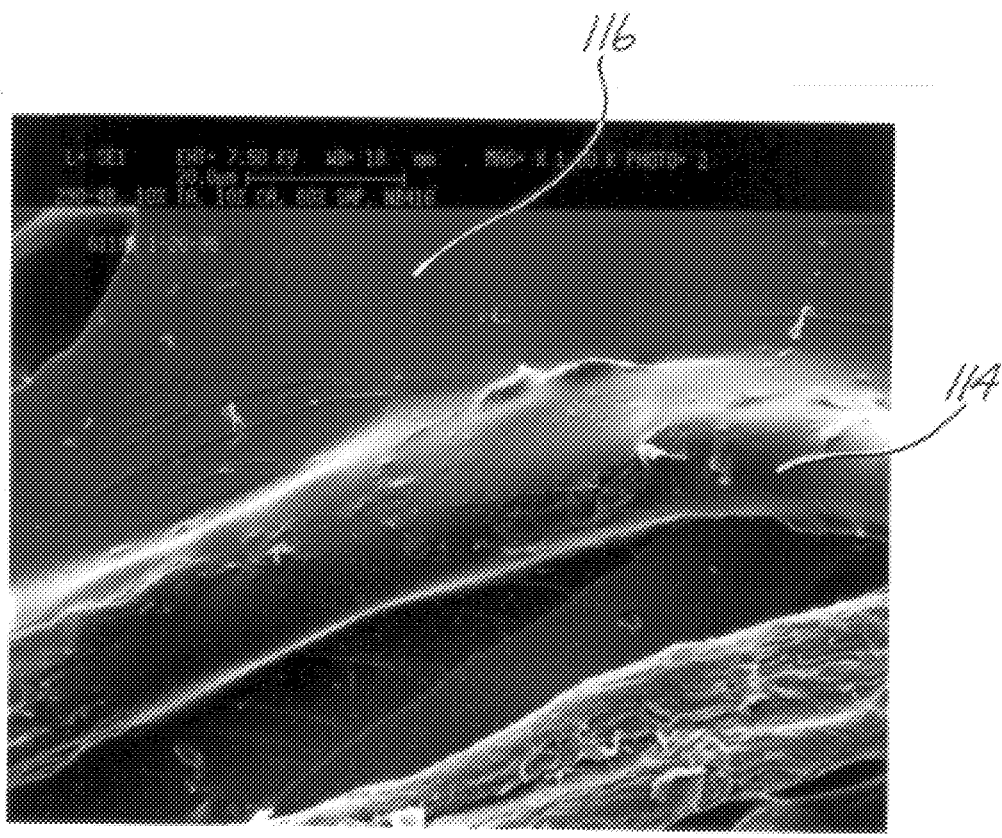
FIG. 10 is a photomicrograph that is an enlargement of FIG. 9 showing the cellulose acetate fibers bonded to superabsorbent particles.

Referring to FIGS. 9 and 10 (which is an enlargement of a region of FIG. 9), a cellulose fiber 112, a cellulose acetate fiber 114, and a large particle 116 of superabsorbent polymer are shown. The cellulose acetate fiber has been partially solubilized and has flowed onto the surface of the SAP (superabsorbent polymer) particle, thus adhering to it. Another cellulose acetate fiber 118 has flowed onto the surface of the cellulose fiber 112 and adhered to it. In this manner, an interlocked web of fibers and particles is formed that results in a product having good integrity.

While preferred embodiments of the invention have been illustrated and described, it will be appreciated that various changes can be made therein without departing from the spirit and scope of the invention.

The embodiments of the invention in which an exclusive property or privilege is claimed are defined as follows:

1. An article comprising:

a web of pulped cellulosic fibers, said fibers being interspersed with each other;

a bonding medium for bonding at least some of said cellulosic fibers to the bonding medium; and a solvent for said bonding medium, said cellulosic fibers being insoluble in said solvent, said bonding medium when contacted with said solvent at least partially solubilizing the medium and rendering it tacky so that said bonding medium adheres to itself and to at least some of said cellulosic fibers, said solvent being present in an amount insufficient to completely solubilize the bonding medium, said solvent after partially solubilizing the surface of the bonding medium thereafter being sufficiently dissipated so that said bonding medium can resolidify, thereby bonding the medium to itself and to at least some of the cellulosic fibers, wherein the bonding medium is coated on fibers that are insoluble in said solvent, the medium coated fibers being interspersed throughout said web.

2. The article of claim 1 wherein the bonding fibers are finish free.

3. The article of claim 1 wherein the solvent and at least some cellulosic fibers are first combined, and thereafter the bonding medium and the solvent and cellulosic fibers are combined to form a hydrophilic bonded web.

4. The article of claim 1 wherein the cellulosic fibers and bonding fibers are first combined to form a blend sheet, and wherein the solvent is thereafter added.

5. The article of claim 1 wherein the solvent is added during or after the time when the cellulosic fibers and bonding fibers are combined.

6. The article of claim 1 wherein the bonding medium comprises particles interspersed throughout said web.

7. The article of claim 1 wherein said bonding medium comprises cellulose acetate, cellulose butyrate, cellulose propionate, cellulose nitrate, vinyl chloride/vinyl acetate copolymer, acetylated pulp fibers, or mixtures thereof.

8. The article of claim 7 wherein the solvent comprises triacetin, triethyl citrate, propane diol diacetate, propane diol dipropionate, propane diol dibutyrate, or mixtures thereof.

9. The article of claim 8 further comprising a particulate additive interspersed throughout the web, the additive being present before the bonding medium resolidifies so that it is bonded to the bonding medium.

10. The article of claim 9 wherein the additive comprises superabsorbent polymers, clay, titanium dioxide, sodium bicarbonate, zeolites, activated carbon, or mixtures thereof.

11. The article of claim 10 wherein the superabsorbent polymers are pretreated by adding solvent thereto prior to combining the superabsorbent polymers into the web.

12. The article of claim 10 in a diaper.

13. The article of claim 10 in an adult incontinence product.

14. The article of claim 10 in a feminine hygiene product.

15. The article of claim 8 wherein the web has a density ranging from about 0.03 g/cc to about 1 g/cc.

16. The article of claim 1 further comprising a particulate additive interspersed throughout the web, the additive being present before the bonding medium resolidifies and being bonded to the bonding medium.

17. The article of claim 16 wherein the additive comprises superabsorbent polymers, clay, titanium dioxide, sodium bicarbonate, zeolites, activated carbon, or mixtures thereof.

18. The article of claim 16 wherein the superabsorbent polymers are pretreated by adding solvent thereto prior to combining the superabsorbent polymers into the web.

19. The article of claim 16 wherein the web has a density ranging from about 0.03 g/cc to about 1 g/cc.

20. The article of claim 1 in a diaper.

21. The article of claim 1 in an adult incontinence product.

22. The article of claim 1 in a feminine hygiene product.

23. The article of claim 1 wherein the bonding medium is further applied to the surface of the web of cellulosic fibers.

24. The article of claim 1 wherein the bonding fibers are substantially straight.

25. A fibrous web comprising:
loosely entangled pulped cellulosic and second fibers, said second fibers having an inner core and an outer coating, said cellulosic and second fibers being uniformly distributed throughout the web;
a solvent,
said cellulosic fibers being insoluble in said solvent;
said outer coating of said second fibers being at least partially soluble in said solvent;
said solvent being present in an amount sufficient to partially solubilize said outer coating of said second fibers and cause said outer coating of said second fibers to bond to at least some of said cellulosic fibers, said solvent being present in an amount insufficient to completely solubilize said outer coating of said second fibers, said solvent being dissipated after partially solubilizing said outer coating of said second fibers so that said partially solubilized outer coating can resolidify.

26. The web of claim 25 wherein said second fibers comprise cellulose acetate, cellulose butyrate, cellulose propionate, cellulose nitrate, vinyl chloride/vinyl acetate copolymer, acetylated pulp fibers, or mixtures thereof.

27. The web of claim 26 wherein the solvent comprises triacetin, triethyl, citrate, propane diol diacetate, propane diol dipropionate, propane diol dibutyrate, or mixtures thereof.

28. The web of claim 27 wherein the web has a density ranging from about 0.03 g/cc to about 1 g/cc.

29. The web of claim 28 further comprising particulate additives interspersed throughout the web, the additives being bonded to the second fibers.

30. The web of claim 29 wherein the additives are superabsorbent polymers, clay, titanium dioxide, sodium bicarbonate, zeolites, activated carbon or mixtures thereof.

31. A method of making an article having improved integrity characteristics comprising:
combining a bonding medium with pulped cellulosic fibers to form a mass of fibers and medium that are loosely interspersed with each other; p1 thereafter introducing a solvent for said bonding medium into said mass of fibers and medium, said cellulosic fibers being insoluble in said solvent, said bonding medium when contacted with said solvent at least partially solubilizing the bonding medium and rendering it tacky so that said bonding medium adheres to itself and to at least some of said cellulosic fibers, said solvent being present in an amount insufficient to completely solubilize the bonding medium, said solvent after partially solubilizing the surface of the bonding medium being sufficiently dissipated so that the surface of said bonding medium can resolidify, thereby permanently bonding the medium to itself and to at least some of the cellulosic fibers, wherein said bonding medium comprises second fibers.

32. The method of claim 31 wherein said solvent is added to at least some of said cellulosic fibers before said second fibers are combined with said at least some of cellulosic fibers.

33. The method of claim 32 wherein the solvent comprises triacetin, triethyl citrate, propane diol diacetate, propane diol dipropionate, propane diol dibutyrate, or mixtures thereof.

34. The method of claim 31 wherein at least some of said solvent is added to said second fibers before said second fibers are combined with said cellulosic fibers.

35. The method of claim 31 wherein said solvent is added during or after the time the cellulosic fibers and second fibers are combined.

36. The method of claim 31 wherein said bonding medium comprises cellulose acetate, cellulose butyrate, cellulose propionate, cellulose nitrate, vinyl chloride/vinyl acetate copolymer, acetylated pulp fibers, or mixtures thereof.

37. The method of claim 31 wherein the solvent comprises triacetin, triethyl citrate, propane diol diacetate, propane diol dipropionate, propane diol dibutyrate, or mixtures thereof.

38. A method of making an article having improved integrity characteristics comprising:

combining a solvent for a bonding medium with pulped cellulosic fibers to form a solvent containing mass of fibers;

introducing a bonding medium into said mass of fibers to form a mass of fibers and bonding medium, said fibers being loosely interspersed, said cellulosic fibers being insoluble in said solvent, said bonding medium when contacted with said solvent at least partially solubilizing the medium and rendering it tacky so that said bonding medium adheres to itself and to at least some of said cellulosic fibers, said solvent being present in an amount insufficient to completely solubilize the bonding medium, said solvent after partially solubilizing the surface of the bonding medium being sufficiently disposed so that the surface of said bonding medium can resolidify, thereby permanently bonding the medium to itself and to at least some of the cellulosic fibers.

39. The method of claim 38 wherein said bonding medium comprises second fibers.

40. The method of claim 38 wherein said bonding medium comprises cellulose acetate, cellulose butyrate, cellulose propionate, cellulose nitrate, vinyl chloride/vinyl acetate copolymer, acetylated pulp fibers or mixtures thereof.

41. A method of making an article having improved integrity characteristics comprising:

introducing a sheet containing pulped cellulosic fibers into a defiberizer;

introducing a sheet containing bonding fibers into the defiberizer;

introducing a solvent for the bonding fibers into at least some of the cellulosic fibers before introducing the cellulosic fibers into the defiberizer, the cellulosic fibers being insoluble in the solvent;

defiberizing the fibers to form a fluff of evenly dispersed cellulosic fibers and bonding fibers and to distribute the solvent evenly throughout the fluff, forming a loose web from said fluff;

said bonding fibers when contacted with said solvent at least partially solubilizing the surface of the bonding fibers and rendering it tacky so that said bonding fibers adhere to themselves and to at least some of said cellulosic fibers, said solvent being present in an amount insufficient to completely solubilize the bonding fibers, said solvent after partially solubilizing the surface of the bonding fibers being sufficiently dissipated so that the surface of said bonding fibers can resolidify, thereby permanently bonding the bonding fibers to themselves and to at least some of the cellulosic fibers.

42. The method of claim 41 wherein the solvent is combined with the bonding fibers before the sheet thereof is introduced into the defiberizer.

43. The method of claim 42 wherein said bonding medium comprises cellulose acetate, cellulose butyrate, cellulose propionate, cellulose nitrate, vinyl chloride/vinyl acetate copolymer, acetylated pulp fibers, or mixtures thereof.

44. The method of claim 42 wherein the solvent comprises triacetin, triethyl citrate, propane diol diacetate, propane diol dipropionate, propane diol dibutyrate, or mixtures thereof.

45. The method of claim 41 wherein said bonding medium comprises cellulose acetate, cellulose butyrate, cellulose nitrate, cellulose propionate, vinyl chloride/vinyl acetate copolymer, polyvinyl acetate, acetylated pulp fibers, or mixtures thereof.

46. The method of claim 41 wherein the solvent is triacetin, triethyl citrate, propane diol diacetate, propane diol dipropionate, propane diol dibutyrate, or mixtures thereof.

47. The method of claim 41 wherein the solvent is added at the time or after both of the cellulosic fibers and bonding fibers are introduced into the defiberizer.

48. The method of claim 41 wherein said bonding medium comprises cellulose acetate, cellulose butyrate, cellulose nitrate, cellulose propionate, vinyl chloride/vinyl acetate copolymer, acetylated pulp fibers, or mixtures thereof.

49. The method of claim 48 wherein the solvent comprises triacetin, triethyl citrate, propane diol diacetate, propane diol dipropionate, propane diol dibutyrate, or mixtures thereof.

50. An article comprising:

a backing sheet;

an overlying storage layer comprising a web of pulped cellulosic fibers, said web including a bonding medium for bonding at least some of said cellulosic fibers to the bonding medium and a solvent for said bonding medium, said cellulosic fibers being insoluble in said solvent, said bonding medium when contacted with said solvent at least partially solubilizing the medium and rendering it tacky so that said bonding medium adheres to itself and to at least some of said cellulosic fibers, said solvent being present in an amount insufficient to completely solubilize the bonding medium, said solvent after partially solubilizing the surface of the bonding medium thereafter being sufficiently dissipated so that bonding medium can resolidify, thereby bonding the medium to itself and to at least some of the cellulosic fibers; and a facing sheet overlying said web.

51. The article of claim 50 wherein said bonding medium comprises second fibers interspersed throughout said web.

52. The article of claim 51 further comprising an acquisition layer comprising a second web of cellulosic fibers lying between said facing sheet and said web.

53. The article of claim 52 wherein said acquisition layer comprises a bonding medium for bonding at least some of said cellulosic fibers to the bonding medium; and a solvent for said bonding medium, said cellulosic fibers being insoluble in said solvent, said bonding medium when contacted with said solvent at least partially solubilizing the medium and rendering it tacky so that said bonding medium adheres to itself and to at least some of said cellulosic fibers, said solvent being present in an amount insufficient to completely solubilize the bonding medium, said solvent after partially solubilizing the surface of the bonding medium thereafter being sufficiently dissipated so that said bonding medium can resolidify, thereby bonding the medium to itself and to at least some of the cellulosic fibers.

54. The article of claim 53 wherein the bonding medium comprises second fibers interspersed throughout the acquisition layer.

55. The article of claim 54 wherein the second fibers comprise cellulose acetate, cellulose butyrate, cellulose propionate, cellulose nitrate, vinyl chloride/vinyl acetate copolymer, acetylated pulp fibers, or mixtures thereof and wherein the solvent comprises triacetin, triethyl citrate, propane diol diacetate, propane diol dipropionate, propane diol dibutyrate, or mixtures thereof.

56. The article of claim 52 wherein the second fibers comprise cellulose acetate, cellulose butyrate, cellulose propionate, cellulose nitrate, vinyl chloride/vinyl acetate copolymer, acetylated pulp fibers, or mixtures thereof and wherein the solvent comprises triacetin, triethyl citrate, propane diol diacetate, propane diol dipropionate, propane diol dibutyrate, or mixtures thereof.

57. An absorbent article comprising:
a liquid impervious backing layer; and
a storage layer overlying said backing layer, said storage layer comprising a liquid pervious tissue overlying a web of pulped cellulosic fibers, said tissue being on the opposite side of said web from said backing layer, said cellulosic fibers being loosely interspersed with each other, a bonding medium for bonding at least some of said cellulosic fibers to the bonding medium, and a solvent for said bonding medium, said cellulosic fibers being insoluble in said solvent, said bonding medium when contacted with said solvent at least partially solubilizing the medium and rendering it tacky so that said bonding medium adheres to itself and to at least some of said cellulosic fibers, said solvent being present in an amount insufficient to completely solubilize the bonding medium, said solvent after partially solubilizing the surface of the bonding medium thereafter being sufficiently dissipated so that said bonding medium can resolidify, thereby bonding the medium to itself and to at least some of the cellulosic fibers.

58. The article of claim 57 wherein said bonding medium comprises second fibers interspersed throughout the web.

59. The article of claim 58 wherein the second fibers comprise cellulose acetate, cellulose butyrate, cellulose propionate, cellulose nitrate, vinyl chloride/vinyl acetate copolymer, acetylated pulp fibers, or mixtures thereof and wherein the solvent comprises triacetin, triethyl citrate, propane diol diacetate, propane diol dipropionate, propane diol dibutyrate, or mixtures thereof.

60. An absorbent article comprising:
a backing sheet;
a storage layer comprising a web of fibers overlying said storage layer;
an upper layer comprising a web of fibers overlying said storage layer;
an intermediate layer interposed between said storage layer and said upper layer comprising a web of pulped cellulosic fibers, said cellulosic fibers being loosely interspersed with each other, a bonding medium for bonding at least some of said cellulosic fibers to the bonding medium, and a solvent for said bonding medium, said cellulosic fibers being insoluble in said solvent, said bonding medium when contacted with said solvent at least partially solubilizing the medium and rendering it tacky so that said bonding medium adheres to itself and to at least some of said cellulosic fibers, said solvent being present in an amount insufficient to completely solubilize the bonding medium, said solvent after partially solubilizing the surface of the bonding medium thereafter being sufficiently dissipated so that said bonding medium can resolidify, thereby bonding the medium to itself and to at least some of the cellulosic fibers; and
a facing layer overlying said upper layer.

61. The article of claim 60 wherein said bonding medium comprises second fibers interspersed throughout said web.

62. The article of claim 61 wherein the second fibers comprise cellulose acetate, cellulose butyrate, cellulose propionate, cellulose nitrate, vinyl chloride/vinyl acetate copolymer, acetylated pulp fibers, or mixtures thereof and wherein the solvent comprises triacetin, triethyl citrate, propane diol diacetate, propane diol dipropionate, propane diol dibutyrate, or mixtures thereof.

* * * * *

UNITED STATES PATENT AND TRADEMARK OFFICE
CERTIFICATE OF CORRECTION

PATENT NO.    : 5,837,627
DATED         : November 17, 1998
INVENTOR(S)   : Donald D. Halabisky et al.

It is certified that error appears in the above-identified patent and that said Letters Patent is hereby corrected as shown below:

Column 4,
Line 29, after solvent, add -- a --.

Column 5,
Line 61, "toll" should read -- roll --.

Column 13,
Line 44, "g/2" should read -- $g/m^2$ --.

Column 15,
Line 33, "1/841" should read -- 1/8 --.

Column 18,
Line 26, after "that" add -- it --.
Line 34, after "weight" add -- based on the pulp weight -- before the period.

Column 26,
Line 23, delete "," after "triethyl".
Line 38, delete "p1" and begin a new paragraph with the word -- thereafter --.

Column 27,
Line 26, "disposed" should read -- dissipated --.

Signed and Sealed this

Twenty-sixth Day of February, 2002

Attest:

JAMES E. ROGAN
*Attesting Officer*     *Director of the United States Patent and Trademark Office*